United States Patent [19]

Yu et al.

[11] Patent Number: 6,043,085
[45] Date of Patent: Mar. 28, 2000

[54] EHRLICHIA CANIS 120-KDA IMMUNODOMINANT ANTIGENIC PROTEIN AND GENE

[75] Inventors: Xue-Jie Yu; David H. Walker, both of Galveston, Tex.

[73] Assignee: Research Development Foundation, Carson City, Nev.

[21] Appl. No.: 09/141,047

[22] Filed: Aug. 27, 1998

[51] Int. Cl.[7] .............................. C12N 15/00; C12N 1/20; C12N 1/14; C12N 1/16
[52] U.S. Cl. .................. 435/325; 435/69.1; 435/70.1; 435/71.1; 435/71.2; 435/320.1; 435/455; 435/326; 435/410; 435/252.3; 435/254.11; 435/252.33; 435/255.1; 435/362; 530/350; 536/23.1; 536/23.5; 536/23.7; 536/24.2
[58] Field of Search .............................. 530/350; 435/325, 435/326, 69.1, 70.1, 71.1, 71.2, 320.1, 455, 410, 252.3, 254.11, 252.33, 255.1, 362; 536/23.1, 23.5, 23.7, 24.2

[56] References Cited

PUBLICATIONS

Chen et al. Clin. Diagn. Lab. Immunol. 4(6)=731–735, Nov. 1997.
Shankarpappa Int. J. Syst. Bacteriol. 42(1)=127–132, Jan. 1992.
Reddy Biochem. Biophy. Res. Communi. 247=636–643, Jun. 29, 1998.
Burgess J. Cell Bio. 111=2130–2138, 1990.
Rudinger Peptid Hormones edited by Parsons J.A. University Park Press, Jun. 1976.
Lazar Mole. Cellu. Biolo. 8(3)=1247–1252, 1988.
Campbell Lab. Tech. Biochem. Molec. Biolo. vol. 23 edited by van der Vliet, 1991.

Primary Examiner—Anthony C. Caputa
Assistant Examiner—Li Lee
Attorney, Agent, or Firm—Benjamin Aaron Adler

[57] ABSTRACT

The present invention provides a 120-kDa protein gene of *Ehrlichia canis*, amplified by PCR using primers derived from the DNA sequences flanking the *Ehrlichia chaffeensis* 120-kDa protein gene. The recombinant *E. canis* 120-kDa protein contains 14 tandem repeat units with 36 amino acids each. The repeat units are hydrophilic and predicted to be surface-exposed. Also disclosed is that the recombinant *E. canis* 120-kDa protein is antigenic and reacts with sera from dogs convalescent from canine ehrlichiosis.

5 Claims, 13 Drawing Sheets

| Primer | Sequence | Position | |
|---|---|---|---|
| pxcf2-2: | GAA ACA ATC TAC CGG GCA TAC | -341 - -321 | (SEQ ID NO: 1) |
| pxcf3: | GAG AAT TGA TTG TGG AGT TGG | -110 - -56 | (SEQ ID NO: 2) |
| pxcf3b: | CAG CAA GAG CAA GAA GAT GAC | 38 - 59 | (SEQ ID NO: 3) |
| pxar5; | ATC TTT CTC TAC AAC CGG | 1258 - 1237 | (SEQ ID NO: 4) |
| pxar4: | ACA TAA CAT TCC ACT TTC AAA | 1454 - 1433 | (SEQ ID NO: 5) |
| pxar3; | AAA CAA AAA AAT AGC AAG CAA | +49 - +70 | (SEQ ID NO: 6) |

-340 AAACAATCTACCGGGCATACTTCAACACAATCAGTATATATTTGCATCTTATGCACTTATCG
-280 GTAACGAAGTGTGTCATTACAGAGTTATTAATAATAAAGTAACCATTTTATTGTAATGT
-220 TTTTCTTGCCAAGTTCAATTAATTATTGTTACATAAGGTATAAATGCGGATTATGGT
-160 TAAATTATGCATGTCGTAAGTATAAAATAAGTTGATAAGTGTTTTGTTATATCCTAATAG
-100 ATATAGGAGGCATTGGTTCTATATATAAATGTTATTTTATGATAATAATTTTAACA
-40 GGATGAATTTGTGCAATGTATTTAAATTAAGAGATTTTTATGGATATTGATAACAATAA 20
          M  D  I  D  N  N  N

TGTGACTACATCAAGTACGCAAGATAAAAGTGGGAATTTAATGGAAGTGATTATGCGTAT 80
 V  T  T  S  S  T  Q  D  K  S  G  N  L  M  E  V  I  M  R  I
ATTAAATTTGGTAATAATTCAGATGAGAAGTAAGCAATGAAGACACTAAAGTTCTTGT 140
 L  N  F  G  N  N  S  D  E  K  V  S  N  E  D  T  K  V  L  V
AGAGAGTTTACAACCTGCTGTGAAGTTAGGACAATGTAGGAAATCCATCAAGTGAAGTTGGTAA 200
 E  S  L  Q  P  A  V  N  D  N  V  G  N  P  S  S  E  V  G  K
AGAAGAAAATGCTCCTGAAGTTAAAGCGGAAGATTTGCAACCTGCTGTAGATGGTAGTGT 260
 E  E  N  A  P  E  V  K  A  E  D  L  Q  P  A  V  D  G  S  V
AGAGAACATTCATCAAGTGAAGTTGGGAAAAAGTATCTGAAACTAGTAAAGAGGAAAGTAC 320
 E  N  I  H  Q  V  K  V  G  K  K  V  S  E  T  S  K  E  E  S  T
TCCTGAAGTTAAAGCAGAAGATTTGCAACCTGCTGTAGATGGTAGTATAGAACATTCATC 380
 P  E  V  K  A  E  D  L  Q  P  A  V  D  G  S  I  E  H  S  S
AAGTGAAGTTGGAGAAGAAAAAGTATCTAAAACTAGTAAAGAGGAAAGTACTCCTGAAGTTAA 440
 S  E  V  G  E  K  V  S  K  T  S  K  E  E  S  T  P  E  V  K
AGCAGAAGATTTGCAACCTGCTGTAGATGATAGTGTGGAACATTCATCAAGTGAAGTTGG 500
 A  E  D  L  Q  P  A  V  D  D  S  V  E  H  S  S  S  E  V  G
AGAAAAAGTATCTGAAACTAGTAAAGAGGAAAATACTCCTGAAGTTAAAGCAGAAGATTT 560
 E  K  V  S  E  T  S  K  E  E  N  T  P  E  V  K  A  E  D  L
GCAACCTGCTGTAGATGGTAGTGTAGAAGTTGGAGAGAAAAAGTATC 620
 Q  P  A  V  D  G  S  S  S  E  V  G  E  K  V  S
TAAAACTAGTAAAGAGGAAAGTACTCCTGAAGTTAAAGCAGAAGATTTGCAACCTGCTGT 680
 K  T  S  K  E  E  S  T  P  E  V  K  A  E  D  L  Q  P  A  V
AGATGATAGTGTGGAACATTCATCAAGTGAAGTTGGAGAGAAAAAGTATCTGAAACTAGTAA 740
 D  D  S  V  E  H  S  S  S  E  V  G  E  K  V  S  E  T  S  K
AGAAGAAAATACTCCTGAAGTTAAAGCGGAAGATTTGCAACCTGCTGTAGATGGTAGTGT 800
 E  E  N  T  P  E  V  K  A  E  D  L  Q  P  A  V  D  G  S  V
AGAACATTCATCAAGTGAAGTTGGGAAAAAGTATCTGAAACTAGTAAAGAGGAAAGTAC 860
 E  H  S  S  S  E  V  G  K  K  V  S  E  T  S  K  E  E  S  T

FIG. 3A

```
TCCTGAAGTTAAAGCAGAAGATTTGCAACCTGCTGTAGATGATAGTGTGGAACATTCATC  920
 P  E  V  K  A  E  D  L  Q  P  A  V  D  D  S  V  E  H  S  S
AAGTGAAGTTGGAGAAAAAGTATCTGAAACTAGTAAAGAGGAAAATACTCCTGAAGTTAG  980
 S  E  V  G  E  K  V  S  E  T  S  K  E  E  N  T  P  E  V  R
AGCAGAAGATTTGCAACCTGCTGTAGATGGTAGTGTAGAAGTACTCCTGAAGTTGAAGTTGG 1040
 A  E  D  L  Q  P  A  V  D  G  S  V  E  H  S  S  E  V  G
AGAAAAAGTATCTGAAACTAGTAAAGAGGAAAGTAAAGTTCATCAAGTTAAAGCAGAAGATTT 1100
 E  K  V  S  E  T  S  K  E  E  S  T  P  E  V  K  A  E  D  L
GCAACCTGCTGTAGATAGTAGTATAGAACATTCATCAAGTGAAGTTGGGAAAAAAGTATC 1160
 Q  P  A  V  D  S  S  I  E  H  S  S  E  V  G  K  K  V  S
TGAAACTAGTAAAGAGGAAAGTACTCCTGAAGTTAAAGCAGAAGATTTGCAACCTGCTGT 1220
 E  T  S  K  E  E  S  T  P  E  V  K  A  E  D  L  Q  P  A  V
AGATGGTAGTGTAGAACATTCATGAAGTTGAAGTTGGAGAAAAAGTATCTGAAACTAGTAA 1280
 D  G  S  V  E  H  S  S  E  V  G  E  K  V  S  E  T  S  K
AGAGGAAAATACTCCTGAAGTTCGAACCTGCTGTAGATGGTAGTGT 1340
 E  E  N  T  P  E  V  K  A  E  D  L  Q  P  A  V  D  G  S  V
AGAACATTCATCAAGTGAAGTTGGAGAAAAAGTATCTGAAACTAGTAAAGAGGAAAATAC 1400
 E  H  S  S  E  V  G  E  K  V  S  E  T  S  K  E  E  N  T
TCCTGAAGTTAAAGCGGAAGATTTGCAACCTGCTGTAGATGGTAGTGTAGAACATTCATC 1460
 P  E  V  K  A  E  D  L  Q  P  A  V  D  G  S  V  E  H  S  S
AAGTGAAGTTGGAGAAAAAGTATCTGAAACTAGTAAAGGAAGAAAGTACTCCTGAAGTTAA 1520
 S  E  V  G  E  K  V  S  E  T  S  K  E  E  S  T  P  E  V  K
```

FIG. 3B

```
AGCGGAAGATTTGCAACCTGCTGTAGATGGTAGTGTGGAACATTCATCAAGTGAAGTTGG  1580
 A  E  D  L  Q  P  A  V  D  G  S  V  E  H  S  S  S  E  V  G
AGAAAAGTATCTGAGACTAGTAAAGAAGAAAGTACTCCTGAAGTTAAAGCGGAAGATT    1640
 E  K  V  S  E  T  S  K  E  E  S  T  P  E  V  K  A  E  D  L
GCAACCTGCTGTAGATGGTAGTGTGGAACATTCATCAAGTGAAGTTGGAGAAAAGTATC   1700
 Q  P  A  V  D  G  S  V  E  H  S  S  S  E  V  G  E  K  V  S
TGAGACTAGTAAAGAGGAAAGTACTCCTGAAGTTAAAGCGGAAGTACAGCCTGTTGCAGA  1760
 E  T  S  K  E  E  S  T  P  E  V  K  A  E  V  Q  P  V  A  D
TGGTAATCCTGTTCCTTTAAATCCTATGCCTTCAATTGATAATATTGATACTAATATAAT  1820
 G  N  P  V  P  L  N  P  M  P  S  I  D  N  I  D  T. N  I  I
ATTCCATTACCATAAAGACTGTAAAAAAGGTTCAGCTGTAGGAACAGATGAAATGTGTTG  1880
 F  H  Y  H  K  D  C  K  K  G  S  A  V  G  T  D  E  M  C  C
TCCTGTATCAGAATTAATGGCTGGGAACATGTTCATATGTATGGAATTTATGTCTATAG   1940
 P  V  S  E  L  M  A  G  E  H  V  H  M  Y  G  I  Y  Y  R
AGTTCAATCAGTAAAGGATTAAGTGGTGTATTTAATATAGATCATTCTACATGTGATTG   2000
 V  Q  S  V  K  D  L  S  G  V  F  N  I  D  H  S  T  C  D  C
TAATTTAGATGTTTATTTTGTAGGATACAATTCTTTTACTAACAAAGAAACAGTTGATT   2060
 N  L  D  V  Y  F  V  G  Y  N  S  F  T  N  K  E  T  V  D  L
AATATAATATTGTAGTACGTAAGCTTTATAAAATTGTATATTGAATAGCAAGTAATGCTA  2120
 I  *  (SEQ ID NO: 7)
ATGCAGTATTGCTTGCTATTTTTTTGTTT (SEQ ID NO: 8)                   2149
```

FIG. 3C

```
Ech   1 MDIDNSNISTADIRSNTDGLIDIIMRILGFGNKNIVQPQDLGSEIYQQEQ  50
        |||||.|:.|.    .  |.::|||||  |||  .  .   . ..:   :
Eca   1 MDIDNNNVTTSSTQDKSGNLMEVIMRILNFGNNSDEKVSNEDTKVLVES.  49

51 EDDTVSQPSLEPFVAESEVSKVEQEKTNPEVLIKDLQDVASHESGVSDQP 100
        ||..     |       |.|.|. |||  .|||       |      :
     50 .....LQPAVNDNVGNPS.SEVGKEENAPEVKAEDLQPAV...DGSVEHS  90

101 AQVVTERENEIESHQGETEKESGITESHKEDEIVSQSSSEPFVAESEVS  150
         .| .:.|    :    |..   :    |  : ||||       .||
     91 SSEVGKKVSETSKEESTPEVKA..EDLQPAVDGSIEHSSSE...VGEKVS 135

151 KVEQEETNPEVLIKDLQDVASHESGVSDQPAQVVTERESEIESHQGETEK 200
        |   .||. |||  .|||             : |    .:|   |  |..  |
    136 KTSKEESTPEVKAEDLQPAV..DDSVEHSSSEV...GEKVSETSKEENTP 180

201 ESGITESHQKEDEIVSQPSSEPFVAESEVSKVEQEETNPEVLIKDLQDVA 300
        |   :     |   :    |||       .|||  .||.  |||  .|||
    181 EVKAEDLQPAVDGSIEHSSSE...VGEKVSKTSKEESTPEVKAEDLQPAV 227

301 SHESGVSDQPAQVVTERESEIESHQGETEKESGITESHQKEDEIVSQPSS 350
         :  |      .:|    |  |. .|    |        :    |  |  ||
    228 ..DDSVEHSSSEV...GEKVSETSKEENTPEVKAEDLQPAVDGSVEHSSS 272

351 EPFVAESEVSKVEQEETNPEVLIKDLQDVASHESGVSDQPAQVVTERESE 400
        |     .||.  .||.  |||  .|||           :  |    .:|      |
    273 E...VGKKVSETSKEESTPEVKAEDLQPAV..DDSVEHSSSEV...GEKV 314

401 IESHQGETEKESGITESHQKEDEIVSQPSSEPFVAESEVSKVEQEKTNPE 450
        |..|    |    :    |    |||        .||. .|..   ||
    315 SETSKEENTPEVRAEDLQPAVDGSVEHSSSE...VGEKVSETSKEESTPE 361

451 ILVEDL 456    (SEQ ID NO: 9)
        :  |||
    362 VKAEDL 367    (SEQ ID NO: 10)
```

FIG. 5

*E. chaffeensis* 120 kDa protein

FIG. 6B

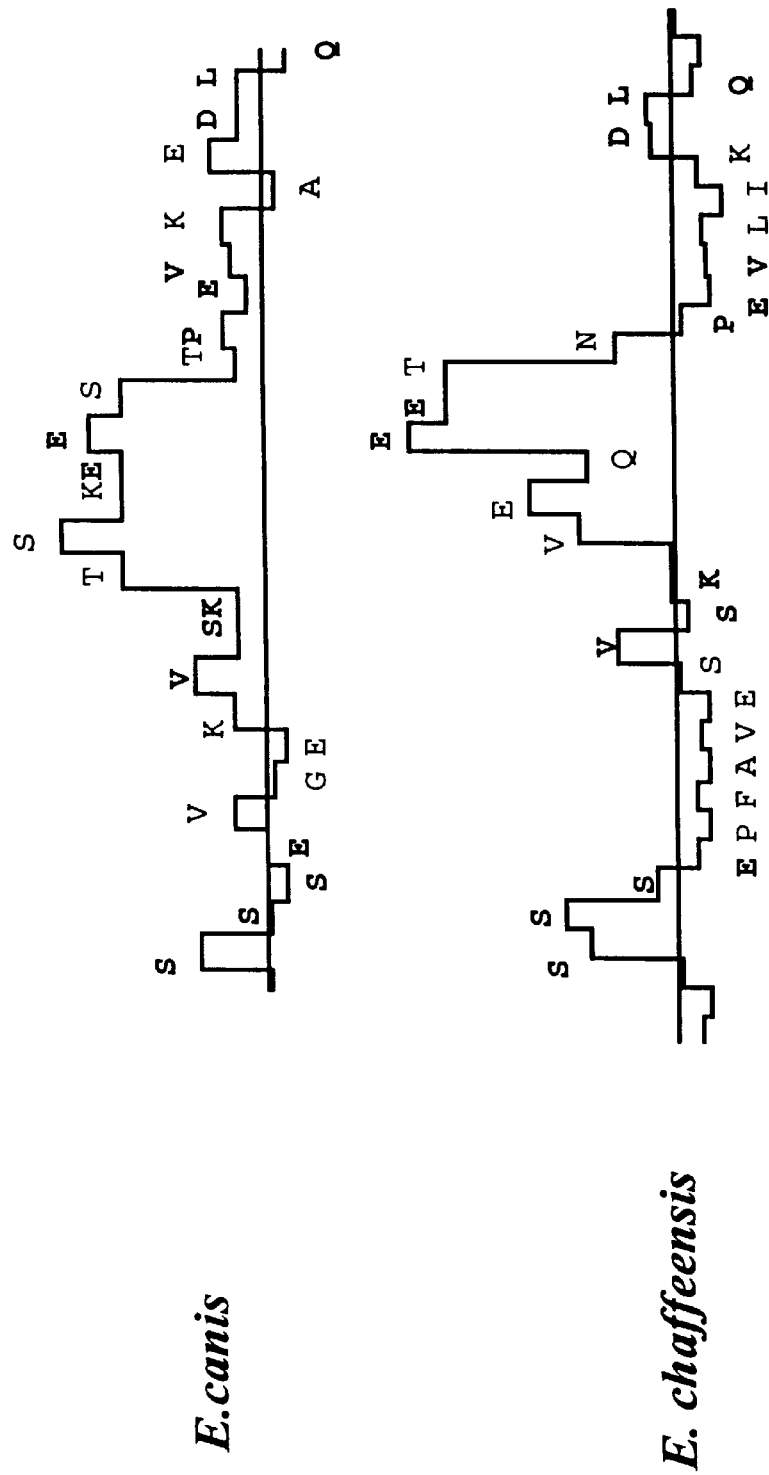

EHRLICHIA CANIS 120-KDA IMMUNODOMINANT ANTIGENIC PROTEIN AND GENE

BACKGROUND OF THE INVENTION

1. Field of the Invention

The present invention relates generally to the fields of molecular biology of parasitic bacteria, particularly agents of rickettsia type diseases and ehrlichial bacteria. More specifically, the present invention relates to molecular cloning and characterization of *Ehrlichia canis* 120-kDa immunoreactive protein gene.

2. Description of the Related Art

Ehrlichia spp. are obligately intracellular gram negative bacteria which reside in the endosome of hematopoietic cells and infect various animal hosts including humans, domestic and wild canidae, deer, horses, sheep, cattle, and wild rodents. Each member of tribe Ehrlichieae has its own particular target cell tropism. Most species of Ehrlichia are either monocytotropic (*E. canis, E. chaffeensis, E. sennetsu, E. risticii,* and *E. muris*) or granulocytotropic (human granulocytic ehrlichia, *E. equi, E. phagocytophila,* and *E. ewingii*) with the exceptions of *Cowdria ruminantium* which grows in the endothelial cells of the host and *Anaplasma marginale*, a red blood cell parasite.

Although ehrlichiae were described in the early part of this century, they received very little attention because they were considered pathogens of only veterinary importance in the United States until this decade. The renewed interest in ehrlichiae is due to the emergence of ehrlichioses affecting humans. In the last decade two new human Ehrlichia pathogens (*E. chaffeensis* and a human *E. phagocytophilia*-like organism) were discovered in the United States (Bakken J. S. 1994, Chen S. M. 1994. JCM, Fishbein D. B., 1987, Maeda, K., 1987). *Ehrlichia canis*, the prototype species of the genus, is the etiologic agent of canine ehrlichiosis, actually only one of five Ehrlichia species that naturally infect dogs. Canine ehrlichiosis is a worldwide disease transmitted by the brown dog tick, *Rhipicephalus sanguineus* (Groves M. G., 1975. Lewis G. E. Jr., 1977). *Ehrlichia canis* causes a mild transient acute febrile illness and may progress to severe illness and a fatal syndrome (tropical canine pancytopenia) (Buhles W. C., 1974, Greene C. E. and J. W. Harvey. 1984, Walker, J. S. 1970). Each year it costs millions of dollars for treating companion and working dogs infected with *E. canis* worldwide. Moreover, *E. canis* also poses a public health threat. *Ehrlichia canis*, or an antigenically indistinguishable organism, was isolated from a human recently (Perez M. 1996).

Understanding the genetic and antigenic composition of *E. canis* is essential for studying the pathogenesis of canine ehrlichiosis and developing an effective vaccine. *Ehrlichia canis* is closely related to *E. chaffeensis* genetically and antigenically (Anderson B. E., 1991, 1992, Chen S. M., 1994. Am J. Trop Med Hyg). Therefore, canine ehrlichiosis may be an appropriate model for studying the pathogenesis of monocytotropic Ehrlichia spp. including *E. chaffeensis*.

The prior art is deficient in the lack of cloning and characterization of immunoreactive gene of *Ehrlichia canis*. Further, the prior art is deficient in the lack of recombinant protein of such immunoreactive gene of *Ehrlichia canis*. The present invention fulfills this long-standing need and desire in the art.

SUMMARY OF THE INVENTION

In one embodiment of the present invention, there is provided a gene encoding a 120 kDa immunoreactive protein of *Ehrlichia canis*. Preferably, the protein has an amino acid sequence of SEQ ID NO: 8 and the gene has a nucleic acid sequence of SEQ ID NO: 7.

In a preferred embodiment of the present invention, there is provided an expression vector comprising a gene encoding a 120 kDa immunoreactive protein of *Ehrlichia canis* and wherein the vector is capable of expressing the gene when the vector is introduced into a cell.

In another embodiment of the present invention, there is provided a recombinant protein comprising an amino acid sequence of SEQ ID NO: 8. Preferably, the amino acid sequence is encoded by a nucleic acid sequence of SEQ ID NO: 7. Preferably, the recombinant protein comprises 14 tandem repeat units with 36 amino acids each. More preferably, the repeat units are hydrophilic. Still more preferably, the recombinant protein is an antigen.

In a preferred embodiment of the present invention, there is provided a method of producing the recombinant protein, comprising the steps of obtaining a vector that comprises an expression region comprising a sequence encoding the amino acid sequence of SEQ ID NO: 8 operatively linked to a promoter; transfecting the vector into a cell; and culturing the cell under conditions effective for expression of the expression region.

The invention may be described in certain embodiments as a method of inhibiting *Ehrlichia canis* infection in a subject comprising the steps of: identifying a subject suspected of being exposed to or infected with *Ehrlichia canis*; and administering a composition comprising a 120 kDa antigen of *Ehrlichia canis* in an amount effective to inhibit an *Ehrlichia canis* infection. The inhibition may occur through any means such as, e.g., the stimulation of the subject's humoral or cellular immune responses, or by other means such as inhibiting the normal function of the 120 kDa antigen, or even competing with the antigen for interaction with some agent in the subject's body.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 5 shows the alignment of the amino acid sequences of the 120-kDa proteins of *E. canis* (SEQ ID NO: 10) and *E. chaffeensis* (SEQ ID NO: 9). Bars represent identical amino acids. Colons indicate conserved replacements.

FIGS. 7A and B shows a comparison of surface-exposed amino acids in a repeat unit of the 120-kDa proteins of *E. canis* and *E. chaffeensis*. FIG. 7A shows the surface probability of amino acids. The corresponding regions were indicated by two arrowheads in FIGS. 6A and B. Bold letters indicated the conserved amino acids between *E. canis* and *E. chaffeensis*. FIG. 7B shows an alignment of the amino acid sequence shown in panel A (SEQ ID NOs: 11–12). Bars represent identical amino acids. Dots represent conserved replacements.

DETAILED DESCRIPTION OF THE INVENTION

Figure 1:
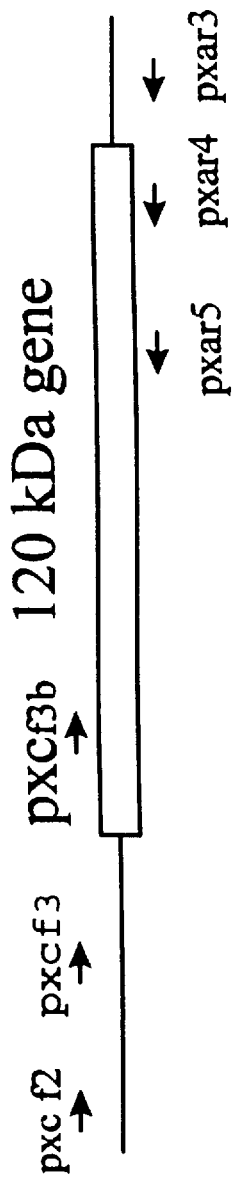
FIG. 1 shows DNA sequences and positions of oligonucleotide primers derived from the *E. chaffeensis* 120-kDa protein gene (open box) and the DNA sequences flanking the gene (line). The positions of primers are indicated as minus and plus for DNA sequences upstream and downstream of the 120-kDa protein gene, respectively. Nine pairs of primers were formed by combining each forward primer (SEQ ID NOs: 1–3) with each reverse primer (SEQ ID NOs: 4–6) and were used to amplify the *E. canis* 120-kDa protein gene by PCR.

In accordance with the present invention there may be employed conventional molecular biology, microbiology, and recombinant DNA techniques within the skill of the art. Such techniques are explained fully in the literature. See, e.g., Maniatis, Fritsch & Sambrook, "Molecular Cloning: A Laboratory Manual (1982); "DNA Cloning: A Practical Approach," Volumes I and II (D. N. Glover ed. 1985); "Oligonucleotide Synthesis" (M. J. Gait ed. 1984); "Nucleic Acid Hybridization" [B. D. Hames & S. J. Higgins eds. (1985)]; "Transcription and Translation" [B. D. Hames & S. J. Higgins eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

Therefore, if appearing herein, the following terms shall have the definitions set out below.

The amino acid described herein are preferred to be in the "L" isomeric form. However, residues in the "D" isomeric form can be substituted for any L-amino acid residue, as long as the desired functional property of immunoglobulin-binding is retained by the polypeptide. $NH_2$ refers to the free amino group present at the amino terminus of a polypeptide. COOH refers to the free carboxy group present at the carboxy terminus of a polypeptide. In keeping with standard polypeptide nomeclature, *J Biol. Chem.*, 243:3552–59 (1969), abbreviations for amino acid residues are shown in the following Table of Correspondence:

| TABLE OF CORRESPONDENCE | | |
|---|---|---|
| SYMBOL | | |
| 1-Letter | 3-Letter | AMINO ACID |
| Y | Tyr | tyrosine |
| G | Gly | glycine |
| F | Phe | Phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| W | Trp | tryptophan |
| R | Arg | arginine |
| D | Asp | aspartic acid |
| N | Asn | asparagine |
| C | Cys | cysteine |

It should be noted that all amino-acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more amino-acid residues. The above Table is presented to correlate the three-letter and one-letter notations which may appear alternately herein.

A "replicon" is any genetic element (e.g., plasmid, chromosome, virus) that functions as an autonomous unit of DNA replication in vivo; i.e., capable of replication under its own control.

A "vector" is a replicon, such as plasmid, phage or cosmid, to which another DNA segment may be attached so as to bring about the replication of the attached segment.

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure herein according to the normal convention of giving only the sequence in the 5' to 3' direction along the nontranscribed strand of DNA (i.e., the strand having a sequence homologous to the mRNA).

An "origin of replication" refers to those DNA sequences that participate in DNA synthesis.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence.

Transcriptional and translational control sequences are DNA regulatory sequences, such as promoters, enhancers, polyadenylation signals, terminators, and the like, that provide for the expression of a coding sequence in a host cell.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site, as well as protein binding domains (consensus sequences) responsible for the binding of RNA polymerase. Eukaryotic promoters often, but not always, contain "TATA" boxes and "CAT" boxes. Prokaryotic promoters contain Shine-Dalgarno sequences in addition to the −10 and −35 consensus sequences.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence.

A "signal sequence" can be included near the coding sequence. This sequence encodes a signal peptide, N-terminal to the polypeptide, that communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes.

The term "oligonucleotide", as used herein in referring to the probe of the present invention, is defined as a molecule comprised of two or more deoxyribonucleotides, preferably more than three. Its exact size will depend upon many factors which, in turn, depend upon the ultimate function and use of the oligonucleotide.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded and must be sufficiently long to prime the synthesis of the desired extension product in the presence of the inducing agent. The exact length of the primer will depend upon many factors, including temperature, source of primer and use of the method. For example, for diagnostic applications, depending on the complexity of the target sequence, the oligonucleotide primer typically contains 15–25 or more nucleotides, although it may contain fewer nucleotides.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence or hybridize therewith and thereby form the template for the synthesis of the extension product.

As used herein, the terms "restriction endonucleases" and "restriction enzymes" refer to enzymes, each of which cut double-stranded DNA at or near a specific nucleotide sequence.

A cell has been "transformed" by exogenous or heterologous DNA when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or ancestor by mitosis. A "cell line" is a clone of a primary cell that is capable of stable growth in vitro for many generations.

Two DNA sequences are "substantially homologous" when at least about 75% (preferably at least about 80%, and most preferably at least about 90% or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. In another example, coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

The labels most commonly employed for these studies are radioactive elements, enzymes, chemicals which fluoresce when exposed to untraviolet light, and others. A number of fluorescent materials are known and can be utilized as labels. These include, for example, fluorescein, rhodamine, auramine, Texas Red, AMCA blue and Lucifer Yellow. A particular detecting material is anti-rabbit antibody prepared in goats and conjugated with fluorescein through an isothiocyanate.

Proteins can also be labeled with a radioactive element or with an enzyme. The radioactive label can be detected by any of the currently available counting procedures. The preferred isotope may be selected from $^3H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$.

Enzyme labels are likewise useful, and can be detected by any of the presently utilized colorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Many enzymes which can be used in these procedures are known and can be utilized. The preferred are peroxidase, β-glucuronidase, β-D-glucosidase, β-D-galactosidase, urease, glucose oxidase plus peroxidase and alkaline phosphatase. U.S. Pat. Nos. 3,654,090, 3,850,752, and 4,016,043 are referred to by way of example for their disclosure of alternate labeling material and methods.

A particular assay system developed and utilized in the art is known as a receptor assay. In a receptor assay, the material to be assayed is appropriately labeled and then certain cellular test colonies are inoculated with a quantitiy of both the label after which binding studies are conducted to determine the extent to which the labeled material binds to the cell receptors. In this way, differences in affinity between materials can be ascertained.

An assay useful in the art is known as a "cis/trans" assay. Briefly, this assay employs two genetic constructs, one of which is typically a plasmid that continually expresses a particular receptor of interest when transfected into an appropriate cell line, and the second of which is a plasmid that expresses a reporter such as luciferase, under the control of a receptor/ligand complex. Thus, for example, if it is desired to evaluate a compound as a ligand for a particular receptor, one of the plasmids would be a construct that results in expression of the receptor in the chosen cell line, while the second plasmid would possess a promoter linked to the luciferase gene in which the response element to the particular receptor is inserted. If the compound under test is an agonist for the receptor, the ligand will complex with the receptor, and the resulting complex will bind the response element and initiate transcription of the luciferase gene. The resulting chemiluminescence is then measured photometrically, and dose response curves are obtained and compared to those of known ligands. The foregoing protocol is described in detail in U.S. Pat. No. 4,981,784.

As used herein, the term "host" is meant to include not only prokaryotes but also eukaryotes such as yeast, plant and animal cells. A recombinant DNA molecule or gene which encodes a 120 kDa immunoreactive protein of Ehrlichia canis of the present invention can be used to transform a host using any of the techniques commonly known to those of ordinary skill in the art. Especially preferred is the use of a vector containing coding sequences for a gene encoding a 120 kDa immunoreactive protein of *Ehrlichia canis* of the present invention for purposes of prokaryote transformation.

Prokaryotic hosts may include *E. coli, S. typhimurium, Serratia marcescens, Mycobacterium vaccae* and *Bacillus subtilis*. Eukaryotic hosts include yeasts such as *Pichia pastoris*, mammalian cells and insect cells.

In general, expression vectors containing promoter sequences which facilitate the efficient transcription of the inserted DNA fragment are used in connection with the host. The expression vector typically contains an origin of replication, promoter(s), terminator(s), as well as specific genes which are capable of providing phenotypic selection in transformed cells. The transformed hosts can be fermented and cultured according to means known in the art to achieve optimal cell growth.

The invention includes a substantially pure DNA encoding a 120 kDa immunoreactive protein of *Ehrlichia canis*, a strand of which DNA will hybridize at high stringency to a probe containing a sequence of at least 15 consecutive nucleotides of (SEQ ID NO:6). The protein encoded by the DNA of this invention may share at least 80% sequence identity (preferably 85%, more preferably 90%, and most preferably 95%) with the nucleic acids listed in FIG. 3 (SEQ ID NO: 7). More preferably, the DNA includes the coding sequence of the nucleotides of SEQ ID NO:8, or a degenerate variant of such a sequence.

The probe to which the DNA of the invention hybridizes preferably consists of a sequence of at least 20 consecutive nucleotides, more preferably 40 nucleotides, even more preferably 50 nucleotides, and most preferably 100 nucleotides or more (up to 100%) of the coding sequence of the nucleotides listed in SEQ ID NO: 8 or the complement thereof. Such a probe is useful for detecting expression of the 120 kDa immunoreactive protein gene of *Ehrlichia canis* in a human cell by a method including the steps of (a) contacting mRNA obtained from the cell with the labeled hybridization probe; and (b) detecting hybridization of the probe with the mRNA.

This invention also includes a substantially pure DNA containing a sequence of at least 15 consecutive nucleotides (preferably 20, more preferably 30, even more preferably 50, and most preferably all) of the region from the nucleotides listed in (SEQ ID NO: 8).

By "high stringency" is meant DNA hybridization and wash conditions characterized by high temperature and low salt concentration, e.g., wash conditions of 65° C. at a salt concentration of approximately 0.1×SSC, or the functional equivalent thereof. For example, high stringency conditions may include hybridization at about 42° C. in the presence of about 50% formamide; a first wash at about 65° C. with about 2×SSC containing 1% SDS; followed by a second wash at about 65° C. with about 0.1×SSC.

By "substantially pure DNA" is meant DNA that is not part of a milieu in which the DNA naturally occurs, by virtue of separation (partial or total purification) of some or all of the molecules of that milieu, or by virtue of alteration of sequences that flank the claimed DNA. The term therefore includes, for example, a recombinant DNA which is incorporated into a vector, into an autonomously replicating plasmid or virus, or into the genomic DNA of a prokaryote or eukaryote; or which exists as a separate molecule (e.g., a cDNA or a genomic or cDNA fragment produced by polymerase chain reaction (PCR) or restriction endonuclease digestion) independent of other sequences. It also includes a recombinant DNA which is part of a hybrid gene encoding additional polypeptide sequence, e.g., a fusion protein. Also included is a recombinant DNA which includes a portion of the nucleotides listed in SEQ ID NO: 8 which encodes an alternative splice variant of a gene encoding a 120 kDa immunoreactive protein of *Ehrlichia canis*.

The DNA may have at least about 70% sequence identity to the coding sequence of the nucleotides listed in SEQ ID NO:8, preferably at least 75% (e.g. at least 80%); and most preferably at least 90%. The identity between two sequences is a direct function of the number of matching or identical positions. When a subunit position in both of the two sequences is occupied by the same monomeric subunit, e.g., if a given position is occupied by an adenine in each of two DNA molecules, then they are identical at that position. For example, if 7 positions in a sequence 10 nucleotides in length are identical to the corresponding positions in a second 10-nucleotide sequence, then the two sequences have 70% sequence identity. The length of comparison sequences will generally be at least 50 nucleotides, preferably at least 60 nucleotides, more preferably at least 75 nucleotides, and most preferably 100 nucleotides. Sequence identity is typically measured using sequence analysis software (e.g., Sequence Analysis Software Package of the Genetics Computer Group, University of Wisconsin Biotechnology Center, 1710 University Avenue, Madison, Wis. 53705).

The present invention comprises a vector comprising a DNA sequence which encodes a gene encoding a 120 kDa immunoreactive protein of *Ehrlichia canis* and said vector is capable of replication in a host which comprises, in operable linkage: a) an origin of replication; b) a promoter; and c) a DNA sequence coding for said protein. Preferably, the vector of the present invention contains a portion of the DNA sequence shown in SEQ ID No: 8. A "vector" may be defined as a replicable nucleic acid construct, e.g., a plasmid or viral nucleic acid. Vectors may be used to amplify and/or express nucleic acid encoding a 120 kDa immunoreactive protein of *Ehrlichia canis*. An expression vector is a replicable construct in which a nucleic acid sequence encoding a polypeptide is operably linked to suitable control sequences capable of effecting expression of the polypeptide in a cell. The need for such control sequences will vary depending upon the cell selected and the transformation method chosen. Generally, control sequences include a transcriptional promoter and/or enhancer, suitable mRNA ribosomal binding sites, and sequences which control the termination of transcription and translation. Methods which are well known to those skilled in the art can be used to construct expression vectors containing appropriate transcriptional and translational control signals. See for example, the techniques described in Sambrook et al., 1989, *Molecular Cloning: A Laboratory Manual* (2nd Ed.), Cold Spring Harbor Press, New York. A gene and its transcription control sequences are defined as being "operably linked" if the transcription control sequences effectively control the transcription of the gene. Vectors of the invention include, but are not limited to, plasmid vectors and viral vectors. Preferred viral vectors of the invention are those derived from retroviruses, adenovirus, adeno-associated virus, SV40 virus, or herpes viruses.

By a "substantially pure protein" is meant a protein which has been separated from at least some of those components which naturally accompany it. Typically, the protein is substantially pure when it is at least 60%, by weight, free from the proteins and other naturally-occurring organic molecules with which it is naturally associated in vivo. Preferably, the purity of the preparation is at least 75%, more preferably at least 90%, and most preferably at least 99%, by weight. A substantially pure 120 kDa immunoreactive protein of *Ehrlichia canis* may be obtained, for example, by extraction from a natural source; by expression of a recombinant nucleic acid encoding a 120 kDa immunoreactive protein of *Ehrlichia canis*; or by chemically synthesizing the protein. Purity can be measured by any appropriate method, e.g., column chromatography such as immunoaffinity chromatography using an antibody specific for a 120 kDa immunoreactive protein of *Ehrlichia canis*, polyacrylamide gel electrophoresis, or HPLC analysis. A protein is substantially free of naturally associated components when it is separated from at least some of those contaminants which accompany it in its natural state. Thus, a protein which is chemically synthesized or produced in a cellular system different from the cell from which it naturally originates will be, by definition, substantially free from its naturally associated components. Accordingly, substantially pure proteins include eukaryotic proteins synthesized in *E. Coli*, other prokaryotes, or any other organism in which they do not naturally occur.

In addition to substantially full-length proteins, the invention also includes fragments (e.g., antigenic fragments) of the 120 kDa immunoreactive protein of *Ehrlichia canis* (SEQ ID No: 7). As used herein, "fragment," as applied to a polypeptide, will ordinarily be at least 10 residues, more typically at least 20 residues, and preferably at least 30 (e.g., 50) residues in length, but less than the entire, intact sequence. Fragments of the 120 kDa immunoreactive protein of *Ehrlichia canis* can be generated by methods known to those skilled in the art, e.g., by enzymatic digestion of naturally occurring or recombinant 120 kDa immunoreactive protein of *Ehrlichia canis*, by recombinant DNA techniques using an expression vector that encodes a defined fragment of 120 kDa immunoreactive protein of *Ehrlichia canis*, or by chemical synthesis. The ability of a candidate fragment to exhibit a characteristic of 120 kDa immunoreactive protein of *Ehrlichia canis* (e.g., binding to an antibody specific for 120 kDa immunoreactive protein of *Ehrlichia canis*) can be assessed by methods described herein. Purified 120 kDa immunoreactive protein of *Ehrlichia canis* or antigenic fragments of 120 kDa immunoreactive protein of *Ehrlichia canis* can be used to generate new antibodies or to test existing antibodies (e.g., as positive controls in a diagnostic assay) by employing standard protocols known to those skilled in the art. Included in this invention are polyclonal antisera generated by using 120 kDa immunoreactive protein of *Ehrlichia canis* or a fragment of 120 kDa immunoreactive protein of *Ehrlichia canis* as the immunogen in, e.g., rabbits. Standard protocols for monoclonal and polyclonal antibody production known to those skilled in this art are employed. The monoclonal antibodies generated by this procedure can be screened for the ability to identify recombinant *Ehrlichia canis* cDNA clones, and to distinguish them from known cDNA clones.

Further included in this invention are fragments of the 120 kDa immunoreactive protein of *Ehrlichia canis* which are encoded at least in part by portions of SEQ ID NO: 7, e.g., products of alternative mRNA splicing or alternative protein processing events, or in which a section of the sequence has been deleted. The fragment, or the intact 120 kDa immunoreactive protein of *Ehrlichia canis*, may be covalently linked to another polypeptide, e.g., which acts as a label, a ligand or a means to increase antigenicity.

The phrase "pharmaceutically acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared. The preparation can also be emulsified.

A protein may be formulated into a composition in a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 mL of isotonic NaCl solution and either added to 1000 mL of hypodermoclysis fluid or injected at the proposed site of infusion, (see for example, "Remington's Pharmaceutical Sciences " 15th Edition, pages 1035–1038 and 1570–1580). Some variation in dosage will necessarily occur depending on the condition of the subject being treated. The person responsible for administration will, in any event, determine the appropriate dose for the individual subject.

As is well known in the art, a given polypeptide may vary in its immunogenicity. It is often necessary therefore to couple the immunogen (e.g., a polypeptide of the present invention) with a carrier. Exemplary and preferred carriers are keyhole limpet hemocyanin (KLH) and human serum albumin. Other carriers may include a variety of lymphokines and adjuvants such as IL2, IL4, IL8 and others.

Means for conjugating a polypeptide to a carrier protein are well known in the art and include glutaraldehyde, m-maleimidobenzoyl-N-hydroxysuccinimide ester, carbodiimide and bis-biazotized benzidine. It is also understood that the peptide may be conjugated to a protein by genetic engineering techniques that are well known in the art.

As is also well known in the art, immunogenicity to a particular immunogen can be enhanced by the use of nonspecific stimulators of the immune response known as adjuvants. Exemplary and preferred adjuvants include complete BCG, Detox, (RIBI, Immunochem Research Inc.) ISCOMS and aluminum hydroxide adjuvant (Superphos, Biosector).

The preparation of vaccines which contain peptide sequences as active ingredients is generally well understood in the art, as exemplified by U.S. Pat. Nos. 4,608,251; 4,601,903; 4,599,231; 4,599,230; 4,596,792; and 4,578,770, all incorporated herein by reference. Typically, such vaccines are prepared as injectables, either as liquid solutions or suspensions: solid forms suitable for solution in, or suspension in, liquid prior to injection may also be prepared. The preparation may also be emulsified. The active immunogenic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the vaccine may contain minor amounts of auxiliary substances such as wetting or emulsifying agents, pH buffering agents, or adjuvants which enhance the effectiveness of the vaccines.

The 120-kDa protein is a potential adhesin of Ehrlichia spp. and is differentially expressed on the surface of densecored cells of *E. chaffeensis*. The gene of *E. canis* was amplified by PCR using primers derived from the DNA sequences flanking the *E. chaffeensis* gene. The *E. canis* gene was cloned, sequenced, and over-expressed in *Escherichia coli*. The 120-kDa protein of *E. canis* contains 14 tandem repeat units with 36 amino acids each. The DNA sequences of the repeats are 94% homologous to one other. The repeat units are hydrophilic and by probability analysis are predicted to be surface-exposed. The overall amino acid sequence of the *E. canis* 120-kDa protein is 30% homologous to the *E. chaffeensis* 120-kDa protein. The repeat regions of the 120-kDa proteins of the two species share common amino acid sequences which are predicted to be surface-exposed. The recombinant *E. canis* 120-kDa protein reacted with sera from dogs convalescent from canine ehrlichiosis.

The present invention is directed to a gene encoding a 120-kDa immunoreactive protein of *Ehrlichia canis* and a recombinant protein encoded by such gene thereof.

In one embodiment of the present invention, there is provided a gene encoding a 120 kDa immunoreactive protein of *Ehrlichia canis*. Preferably, the protein has an amino acid sequence of SEQ ID NO: 8 and the gene has a nucleic acid sequence of SEQ ID NO: 7.

In a preferred embodiment of the present invention, there is provided an expression vector comprising a gene encoding a 120 kDa immunoreactive protein of *Ehrlichia canis* and capable of expressing the gene when the vector is introduced into a cell.

In another embodiment of the present invention, there is provided a recombinant protein comprising an amino acid sequence of SEQ ID NO: 8. Preferably, the amino acid sequence is encoded by a nucleic acid sequence of SEQ ID NO: 7. Preferably, the recombinant protein comprises 14 tandem repeat units with 36 amino acids each. More preferably, the repeat units are hydrophilic. Still more preferably, the recombinant protein is an antigen.

In a preferred embodiment of the present invention, there is provided a method of producing the recombinant protein, comprising the steps of obtaining a vector that comprises an expression region comprising a sequence encoding the amino acid sequence of SEQ ID NO: 8 operatively linked to a promoter; transfecting the vector into a cell; and culturing the cell under conditions effective for expression of the expression region.

As used herein the term "complement" is used to define the strand of nucleic acid which will hybridize to the first nucleic acid sequence to form a double stranded molecule under stringent conditions. Stringent conditions are those that allow hybridization between two nucleic acid sequences with a high degree of homology, but precludes hybridization of random sequences. For example, hybridization at low temperature and/or high ionic strength is termed low stringency and hybridization at high temperature and/or low ionic strength is termed high stringency. The temperature and ionic strength of a desired stringency are understood to be applicable to particular probe lengths, to the length and base content of the sequences and to the presence of formamide in the hybridization mixture.

As used herein, the term "engineered" or "recombinant" cell is intended to refer to a cell into which a recombinant gene, such as a gene encoding an *Ehrlichia chaffeensis* antigen has been introduced. Therefore, engineered cells are distinguishable from naturally occurring cells which do not contain a recombinantly introduced gene. Engineered cells are thus cells having a gene or genes introduced through the hand of man. Recombinantly introduced genes will either be in the form of a cDNA gene, a copy of a genomic gene, or will include genes positioned adjacent to a promoter not naturally associated with the particular introduced gene. In addition, the recombinant gene may be integrated into the host genome, or it may be contained in a vector, or in a bacterial genome transfected into the host cell.

The following examples are given for the purpose of illustrating various embodiments of the invention and are not meant to limit the present invention in any fashion.

EXAMPLE 1

Ehrlichia

*Ehrlichia canis* Oklahoma strain was provided by Dr. Jacqueline Dawson (Centers for Disease Control, Atlanta, Ga.). *E. canis* Florida strain and three North Carolina isolates (Demon, D. J., and Jake) were provided by Dr. Edward B. Breitschwerdt (College of Veterinary Medicine, North Carolina State University, Raleigh, N.C.). *E. canis* Louisiana strain was provided by Dr. R. E. Corstvet (Louisiana State University, Baton Rouge, La.). Ehrlichiae were cultivated in DH82 cells, a canine macrophage-like cell line (Dawson J. E., 1991). DH82 cells were harvested with a cell scraper when 100% of the cells were infected with ehrlichiae. The cells were centrifuged at 17,400×g for 20 min. The pellets were disrupted with a Braun-Sonic 2000 sonicator at 40 W for 30 sec twice on ice. The cell lysate was loaded onto discontinuous gradients of 42%-36%-30% renografin, and then centrifuged at 80,000×g for 60 min. Ehrlichiae in the heavy and light bands were collected (Weiss E., 1975) and washed by centrifugation with sucrose-phosphate-glutamate buffer (SPG, 218 mM sucrose, 3.8 mM KH2PO4, 7.2 mM K2HPO4, 4.9 mM glutamate, pH 7.0).

EXAMPLE 2

DNA Preparation

*Ehrlichia canis* genomic DNA was prepared from renografin density gradient purified ehrlichiae by using an IsoQuick nucleic acid extraction kit (ORCA Research Inc., Bothell, Wash.) according to the instructions of the manufacturer. Plasmid DNA was purified by using a High Pure Plasmid Isolation Kit (Boehringer Mannheim Corp., Indianapolis, Ind.). The PCR product was purified by using a QIAquick PCR Purification kit (QIAGEN Inc., Santa Clarita, Calif.).

EXAMPLE 3

PCR Amplification of the *E. canis* 120-kDa Protein Gene

Primers were designed based on the DNA sequence of the *E. chaffeensis* 120-kDa protein gene (SEQ ID NOs: 1–6, FIG. 1) (Yu, X-J 1996). The *E. canis* 120-kDa protein gene was amplified by PCR with 30 cycles of 94° C. 30 sec, 52° C. min., and 72° C. 2 min. PCR amplified products were cloned into pCR2.1 TA cloning vector (Invitrogen, Carlsbad, Calif.).

EXAMPLE 4

DNA Sequencing

DNA was sequenced with an ABI Prism 377 DNA Sequencer (Perkin-Elmer Applied Biosystems, Foster City, Calif.).

EXAMPLE 5

Unidirectional Deletion of the *E. canis* 120 kDa Protein Gene

The repeat region was deleted from the 5' end of the *E. canis* 120 kDa protein gene by using Spe I restriction endonuclease partial digestion. The pCR120 plasmid was first completely digested with Xba I, which had a unique cleavage site on the plasmid sequence near the 5' end of the *E. canis* 120 kDa protein gene. Then the plasmid was partially digested with Spe I. Spe I had a unique cleavage site in each repeat of the *E. canis* 120 kDa protein gene, but had no cutting site outside the repeat region including the plasmid vector sequence. To ensure an appropriately representative partial digestion, an aliquot was removed from the digestion mixture every 5 min. The digestion was stopped by adding EDTA to a final concentration of 50 mM and heating at 70° C. for 10 min. After complete digestion with Xba I and partial digestion with Spe I, various numbers of repeat units were removed (deleted) between Xba I and each Spe I cleavage site to generate deleted plasmid DNAs with non-compatible ends (Xba I at the 3' end and Spe I at 5' the end). The restriction enzyme digested mixture was treated with Klenow fragment to fill in the ends. The restriction mixture was then separated by electrophoresis on an agarose gel to remove the plasmids from the internal repeats because their molecular sizes differed significantly. The mixture of the deleted plasmids were extracted from the gel by using a QlAquick Gel Extraction Kit (QIAGEN Inc., Santa Clarita) and self-ligated by using T4 ligase. The deleted plasmids were transformed into *E.coli* strain DH5α and selected for sequencing according to their sizes. Alternatively, the repeat region of the *E. canis* 120 kDa protein gene was unidirectionally deleted from the 3' end by using Exonuclease III with the Erase-a-Base System (Promega, Madison, Wis.) according to the instructions of the manufacturer.

EXAMPLE 6

Determining the Number of Repeats in the *E. canis* 120-kDa Protein Gene

The PCR amplified 120 kDa protein gene from all *E. canis* were cloned into pCR2.1 TA Cloning vector (Invitrogen). The recombinant plasmid was first digested completely with EcoR I and then digested partially with Spe I as described above. The digestion mixtures were separated in a 1% agarose gel and vacuum transferred onto a nylon membrane. The DNA bands in the nylon membrane were hybridized with an oligonucleotide probe which was derived from the sequence upstream of the repeat region of the *E. canis* 120-kDa protein gene. The DNA probes were labeled using digoxigenin-11-dUTP with a DIG Oligonucleotide Tailing Kit (Boehringer Mannheim Co., Indianapolis, Ind.) according to the manufacturer's protocol.

EXAMPLE 7

Gene Analysis

DNA sequence and deduced amino acid sequences were analyzed using the Wisconsin GCG software package (Genetic Computer Group, Inc., Madison, Wis.) and DNAS-TAR software (DNASTAR, Inc., Madison, Wis.). The signal sequence of the deduced protein was analyzed by using the PSORT program (World Wide Web site at URL: http://psort.nibb.ac.jp), which predicts the presence of signal sequences by the methods of McGeoch (D. J. McGeoch, Virus Research, 3, 271, 1985) and von Heijne (von Heijne G., 1986. Nucl. Acids Res., 14, 4683.) and detects potential transmembrane domains by the method of Klein et al. (P. Klein, M. Kanehisa, and C. DeLisi, Biochem. Biophys. Acta, 815, 468, 1985).

EXAMPLE 8

Expression of the E. canis 120-kDa Protein Gene in E. coli

Directly cloning the E. canis 120 kDa protein gene into the pGEX expression vector (Amersham Pharmacia Biotech, Piscataway, N.J.) was prevented by the absence of matched restriction endonuclease cleavage sites on both DNA sequences of the 120 kDa protein gene and the multiple cloning site of the pGEX vector. The coding region of the E. canis 120 kDa protein gene from nucleotide 175 to nucleotide 1793 was amplified by using PCR with a forward primer (SEQ ID NO: 13) and a reverse primer (SEQ ID NO: 14). The PCR products were cloned into pCR2.1 TA cloning vector (Invitrogen) to obtain the EcoR I cleavage site on both ends of the insert. The insert in a recombinant pCR2.1 plasmid was cut by EcoR I and separated from the plasmid DNA in an agarose gel. The insert was extracted from agarose gel by using a QIAquick Gel Extraction Kit (QIAGEN Inc., Santa Clarita) and cloned into EcoRI digested PGEX vector. The E. canis protein was expressed in E. coli BL21 strain as a GST-fusion protein. The GST-fusion protein was affinity-purified by using Glutathione Sepharose 4B beads (Amersham Pharmacia Biotech, Piscataway, N.J.). The E. canis 120-kDa recombinant protein was cleaved from the GST-fusion protein with thrombin.

EXAMPLE 9

Immunization of Mice

Mice were immunized with recombinant E. canis 120-kDa protein to produce antisera. The recombinant p120 protein was mixed with an equal volume of Freund's complete adjuvant for the first injection and with Freund's incomplete adjuvant for the subsequent injections. Mice were immunized intraperitoneally or subcutaneously with 50 µg of the recombinant fusion of the 120-kDa protein and GST on each of 4 occasions.

EXAMPLE 10

Detecting of the E. canis 1 20-kDa Protein Gene

Southern blotting was used to attempt to detect the E. canis 120-kDa protein gene. A 1.2 kb DNA fragment amplified from the E. chaffeensis 120-kDa protein gene with PCR primer pair pxcf3b (SEQ ID NO: 3) and pxar4 (SEQ ID NO: 5, FIG. 1) was labeled with digoxigenin-d-UTP and used as a probe to detect the homologous gene in E. canis by Southern blot. Southern blot revealed that the E. chaffeensis 120-kDa protein gene probe failed to hybridize with EcoR I-digested E. canis genomic DNA under conditions in which the probe gave strong hybridization with E. chaffeensis genomic DNA. This result indicated that E. canis 120-kDa protein gene differed substantially from the homologous E. chaffeensis 120-kDa protein gene.

Although the overall similarity of the 120-kDa protein genes of E. canis and E. chaffeensis is low, it was conceivable that they might contain some conserved domains which could be used to design PCR primers that would amplify both 120 kDa protein gene. Therefore, the homologous gene of the 120-kDa protein in E. canis (Oklahoma strain) was further amplified by PCR. Primers derived from the E. chaffeensis 120-kDa protein gene and sequences flanking the gene had been used previously for sequencing the E. chaffeensis 120-kDa protein gene (FIG. 1). Three forward primers (SEQ ID NOs: 1–3) were paired with 3 reverse primers (SEQ ID NOs: 4–6) to form nine pairs of primers. PCR results demonstrated that E. canis DNA was not amplified with primers within the coding region of the E. chaffeensis 120-kDa protein gene. A 2.5 kb DNA fragment was amplified from E. canis genomic DNA by the primer pair, pxcf2-2 and pxar3, derived from the non-coding DNA sequences flanking the 120-kDa protein gene of E. chaffeensis (FIG. 1).

EXAMPLE 11

Determining the Number of Repeat Units in the E. canis 120-kDa Protein Gene

Figures 2A, 2B:
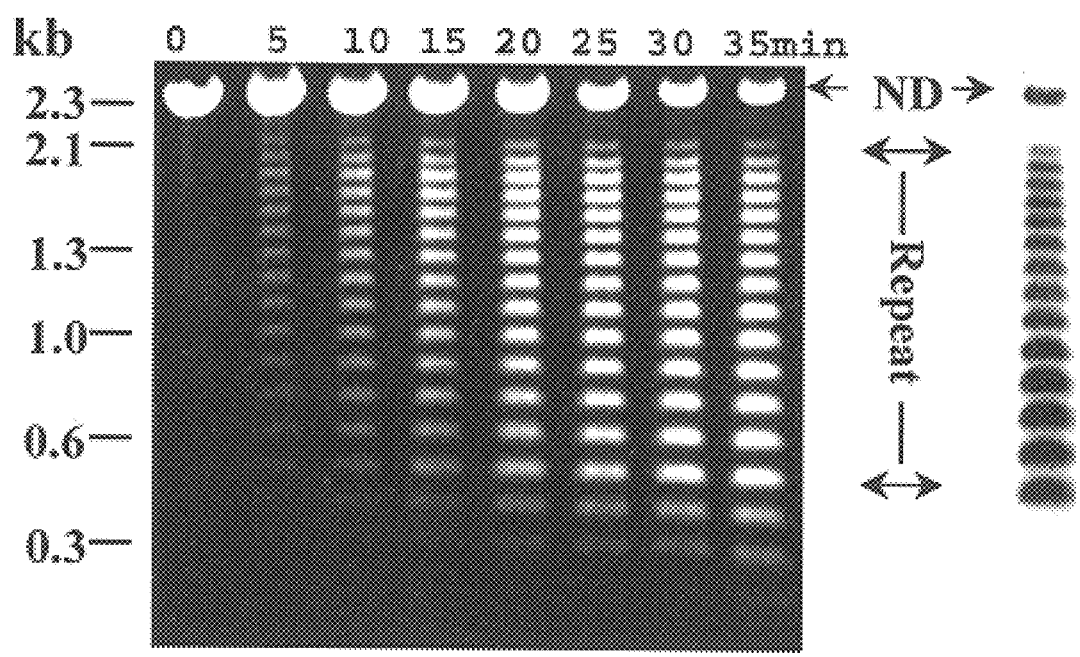
FIG. 2A shows agarose gel electrophoresis of the repeat units of the *E. canis* 120-kDa protein gene. pCA120 was first digested with EcoR I to release the insert and then digested with Spe I at various time points.
FIG. 2B shows a Southern blot determining the number of repeats. DNA digested for 35 minutes with Spe I from the gel in panel A was transferred to a nylon membrane and hybridized with a digoxigenin-labeled oligonucleotide probe which anneals to the DNA sequences upstream of the repeat region of the *E. canis* 120-kDa protein gene. ND=Nondigested DNA FIGS. 3A, B and C show the DNA sequence of the *E. canis* 120-kDa gene (SEQ ID NO: 7) and the deduced amino acids (SEQ ID NO: 8). The nucleic acids of repeats 1, 3, 5, 7, 9, 11, and 13 are underlined.

Southern blot was used to demonstrate how many repeat units the E. canis 120 kDa protein gene had. Restriction enzyme analysis of the DNA sequence of the 120 kDa protein gene of Oklahoma strain demonstrated that all repeats have a unique Spe I endonuclease cleavage site. The insert in the pCR120 plasmid was partially digested with Spe I. Spe I partial digestion of the DNA of E. canis 120-kDa protein gene produced three kinds of DNA fragments: repeats with the 5' end non-repeat sequence, the internal repeats, and the repeats with 3' end non-repeat sequences. After Spe I partial digestion, all DNA fragments with the 5' end non-repeat sequence of the gene started from the same point (5' end of the gene), but finished within the various repeats. These DNA fragments were separated on agarose gel according to their length which corresponded to their repeat numbers. DNAs were transferred to a nylon membrane and used to hybridize with a DIG-labeled oligonucleotide. The oligonucleotide (SEQ ID NO: 15) was derived from the DNA sequences from nucleotide 38 to 59 which were upstream of the repeat region. Therefore, the oligonucleotide hybridized only with the DNA fragments which had the 5' end of the gene, but not with the internal repeats or the repeats with 3' end of the gene. Thus, the number of bands detected by the oligonucleotide probe represents the number of repeats. Southern blotting revealed a ladder of 14 bands with increments of 108 bp in E. canis (FIG. 2). These results indicated that E. canis had 14 repeats with 108 bp each.

EXAMPLE 12

DNA Sequence Analysis of the E. canis 120-kDa Protein Gene

Figure 4:
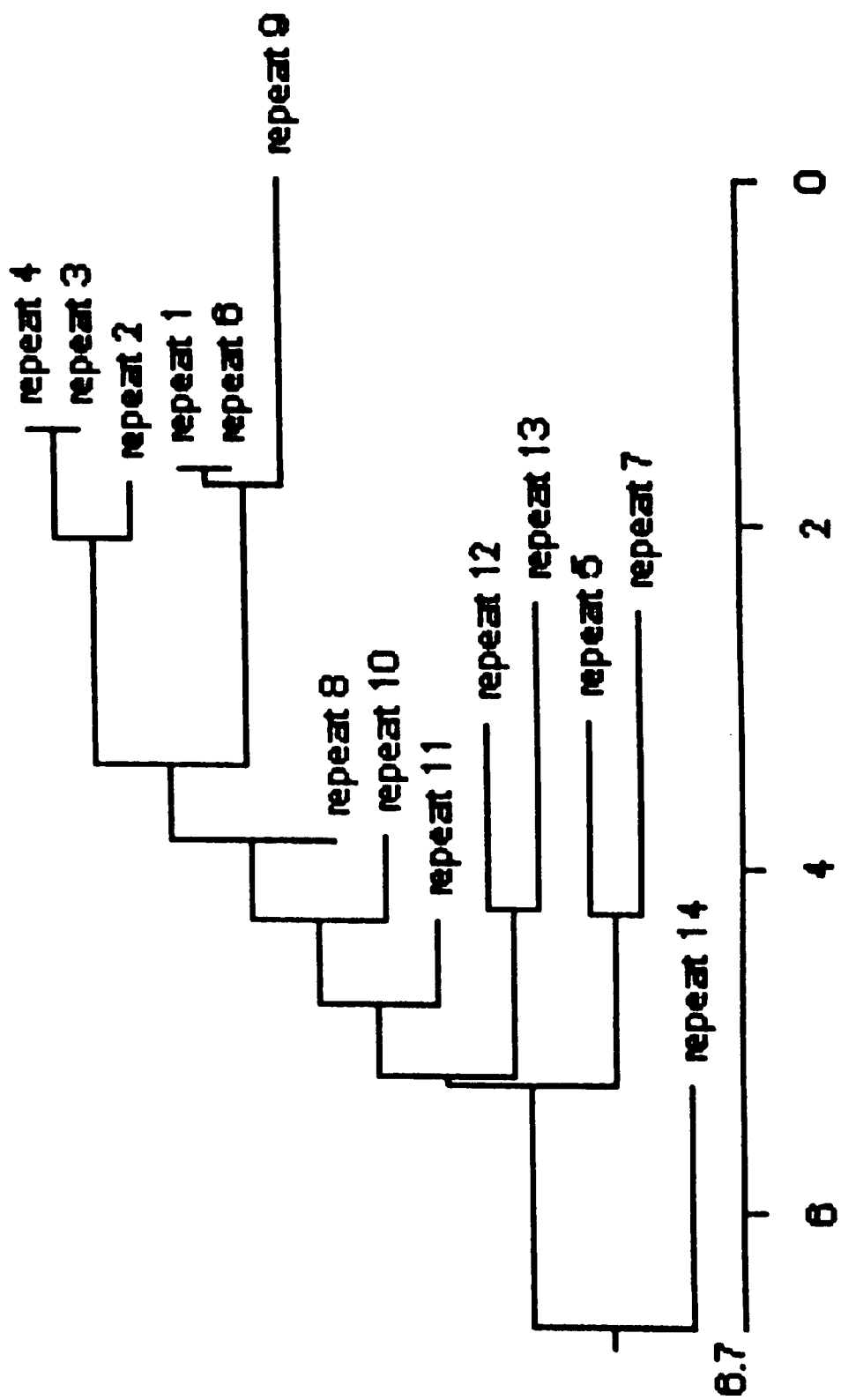
FIG. 4 shows phylogenetic tree of the repeat units of the *E. canis* 120-kDa gene. The scale represents % difference in DNA sequence.

The PCR amplified E. canis DNA fragment was cloned into pCR2.1 vector. The resultant recombinant plasmid was designated as pCA120. The pCA120 plasmid DNA was used as template for sequencing the E. canis DNA insert. DNA sequence was obtained initially by utilizing T7 and M13 reverse primers which were complementary to the vector DNA sequence flanking the insert. Subsequent sequencing of DNA was achieved by primer walking the insert and restriction endonuclease or exonuclease III unidirectional deletion of the insert in pCA120 plasmid. DNA sequence analysis demonstrated that the DNA insert contained an open reading frame (ORF) of 2064 nucleotides (SEQ ID NO: 7) which encoded 688 amino acids (SEQ ID NO: 8). This open reading frame was designated as the 120 kDa protein gene of E. canis. No consensus DNA sequences of E. coli promoter near the 5' end of the gene was found. The N-terminal of the deduced amino acids did not share consensus sequence with E. coli signal peptides. There are 14 tandem repeats in the E. canis 120-kDa protein gene. Each repeat consisted of 108 nucleotides which encoded 36 amino acids each (FIG. 3). The amino acid homology of all repeats were greater than 94% (FIG. 4). Preceding the first repeat there is an incomplete repeat which has a 7 amino acid deletion (FIG. 3) and is 70% homologous to the other repeats.

The FastA program search of the Genbank database revealed that the E. canis 120-kDa protein gene has no significant homology with any known sequence in the database. The amino acid homology of 120-kDa proteins of E. canis (SEQ ID NO: 10) and E. chaffeensis (SEQ ID NO: 9) is 30% (FIG. 5). The 120-kDa proteins are more conserved on their N-terminal and in the repeat region. The amino acid homology is 50% for the first 32 amino acids on the N-terminus of the 120-kDa proteins of E. canis and E. chaffeensis. The DNA sequence homology is 58% for the 120 kDa protein genes of the two species. The non-coding sequence DNA of 340 bp upstream of the E. canis 120-kDa protein gene was sequenced and it was found that the non-coding regions adjacent to the 120-kDa protein genes of the two species of Ehrlichia have 84% homology.

Figure 6A:
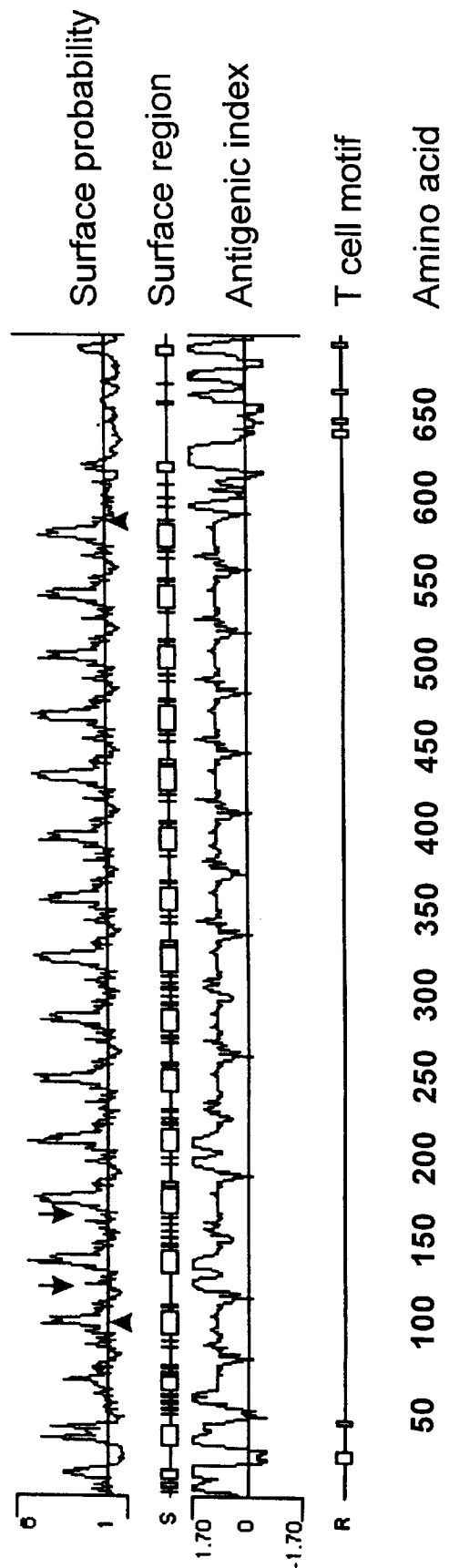
FIGS. 6A and B shows surface probability and hydrophobicity of the 120-kDa proteins of *E. canis* and *E. chaffeensis*. The region between the arrowheads represents the repeat domain. All the repeats in both proteins are hydrophilic and surface-exposed. The second repeat unit of the *E. canis* 120 kDa protein and a peak of the first repeat unit of *E. chaffeensis* 120 kDa protein are present between the two arrows and are magnified in FIGS. 7A and B.
Figure 6B:
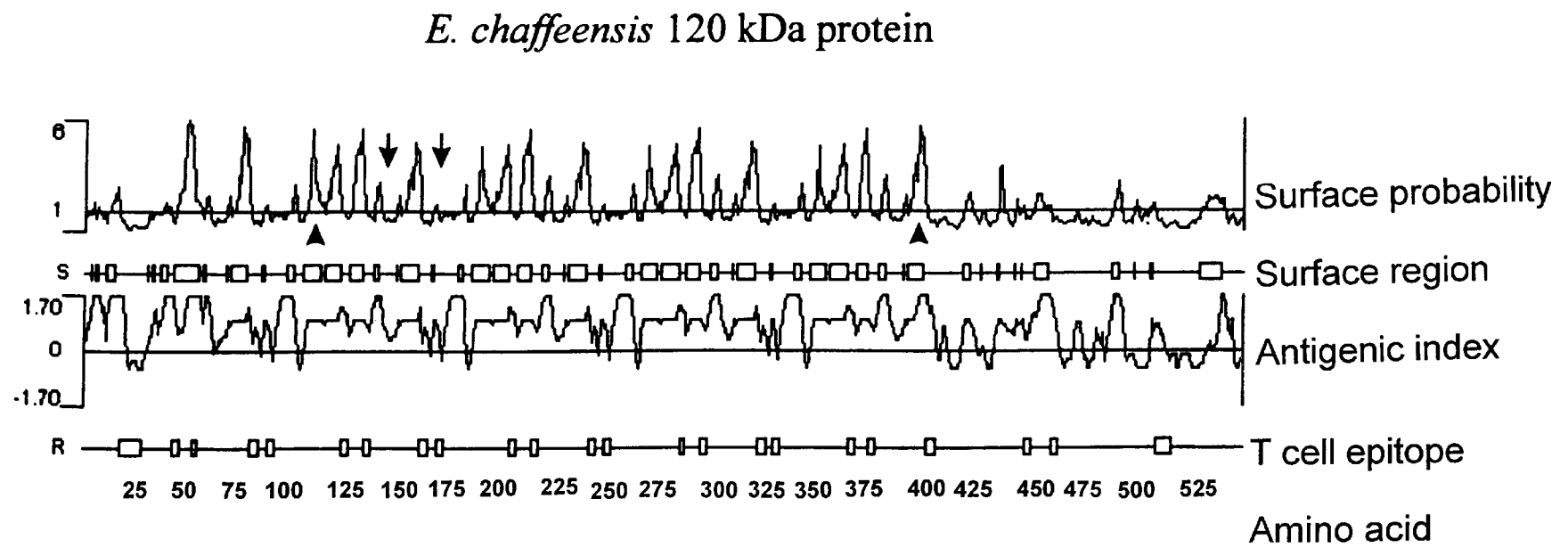

EXAMPLE 13
Predicted Localization and Antigenicity of the E. canis 120-kDa Protein The deduced amino acid sequence of the 120-kDa protein gene of E. canis was analyzed for hydrophobicity, surface probability, and antigenicity with the Protein program of Lasergene software (DNASTRA Inc., Madison, Wis.). All repeat units are predicted to be hydrophilic and surface exposed (FIGS. 6). Comparison of the 120-kDa proteins of E. canis and E. chaffeensis demonstrated that all repeat units in both proteins are predicted to be surface-exposed. The surface-exposed regions of the repeats have common amino acids in the two ehrlichial species (SEQ ID NOs: 11–12, FIG. 7). These results suggest that the 120-kDa protein of E. canis is an outer membrane protein. The hydrophilic amino acids in the repeats may be the surface exposed portions of the protein.

Analysis of proteins with the Jameson-Wolf method which predicts potential antigenic determinants indicated that both E. canis and E. chaffeensis 120 kDa proteins were very likely to be highly antigenic (FIG. 6). Analysis of the proteins with the Rothbard-Taylor method, which locates potential T-lymphocyte antigenic determinants, demonstrated that the E. canis 120 kDa protein had a few predicted T-cell epitopes and all of them located on the sequences outside the repeat domain. In contrast, each repeat of the E. chaffeensis 120 kDa protein had two T-cell epitopes.

EXAMPLE 14
Homologous Genes in Other Strains of E. canis

Figure 8:
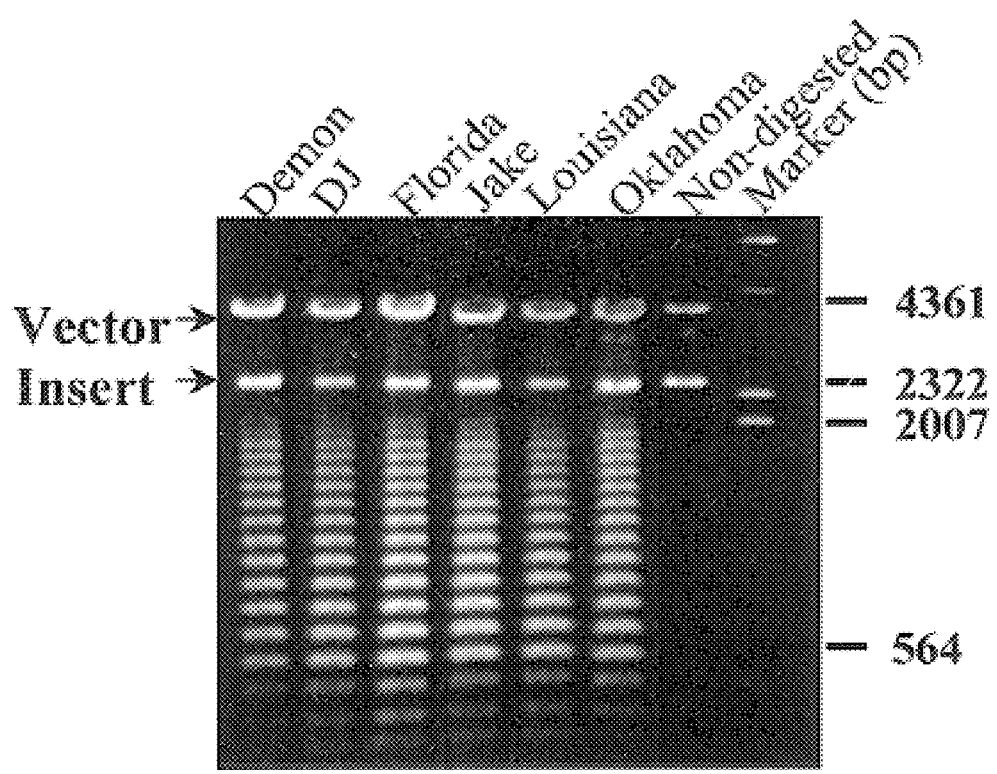
FIG. 8 shows agarose gel electrophoresis of the *E. canis* 120-kDa gene from all *E. canis* strains partially digested with Spe I. The recombinant pCR2.1 plasmids were first digested EcoR I to release the insert from the vector and then digested with Spe I partially. Non-digested: Oklahoma strain 120 kDa gene DNA was digested with EcoR I, but not with Spe I to show the size of the insert.

PCR was used to amplify the 120-kDa protein gene from other strains of E. canis. A 2.5 kb DNA fragment was amplified from all strains of E. canis including strains Florida, Louisiana, and three North Carolina canine isolates: Demon, DJ, and Jake with primers PXCf2-2 and PXAr3. The segments of 120 kDa protein genes of all E. canis strains were sequenced on both the 5' and 3' ends. DNA sequence analysis demonstrated that the DNA sequences up- and downstream of the repeat region were identical among all strains of E. canis. The complete repeat region for all E. canis strains was not sequenced because the gene had to be deleted for sequencing. Only the last repeat of all strains and the first repeat of DJ strain was sequenced. The sequence of the first repeat of DJ and Oklahoma strains was identical. The sequence of the last repeat was identical among all strains. The homology of the 120 kDa protein gene from all E. canis strains was further demonstrated by their identical Spe I restriction physical maps (FIG. 8).

EXAMPLE 15
SDS-PAGE and Western Blot

Figure 9A:
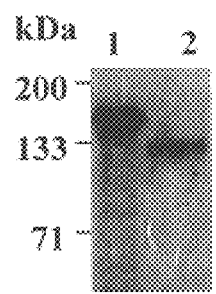
FIG. 9A shows SDS-PAGE of *E. coli*-expressed *E. canis* 120-kDa protein. 1, GST fusion protein; 2, *E. canis* recombinant 120-kDa protein cleaved from the GST fusion protein by thrombin.
Figure 9B:
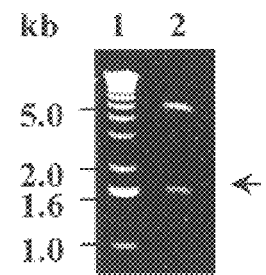
FIG. 9B shows agarose gel electrophoresis of a pGEX plasmid expressing the *E. canis* 120-kDa protein. The insert is indicated by an arrow.
Figure 10:
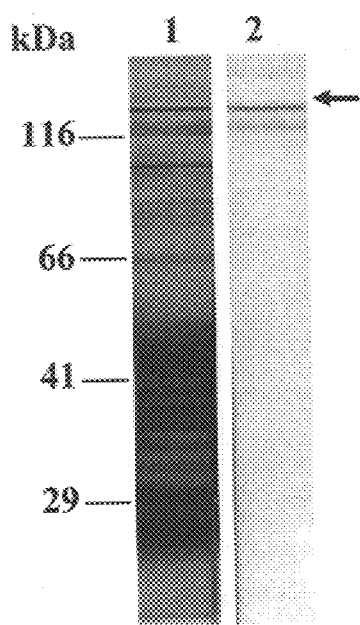
FIG. 10 shows a Western immunoblot of mouse anti-*E. canis* 120-kDa recombinant protein sera reacted with *E. canis* antigen (lane 1) and 120-kDa recombinant protein (lane 2, arrow).
Figure 11:
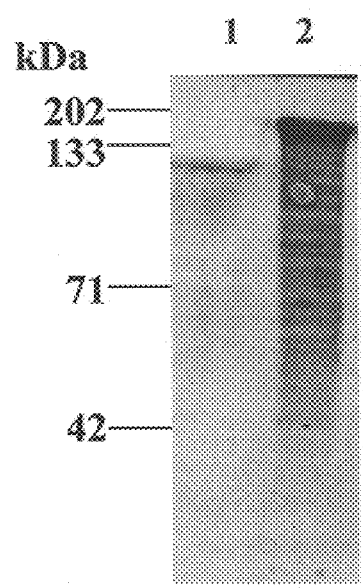
FIG. 11 shows Western blotting of canine convalescent serum reacting with recombinant 120 kDa protein of *E. canis*.

The E. canis 120-kDa protein gene was overexpressed in E. coli (FIG. 9). The recombinant protein encoded by a 1620 bp DNA fragment including the entire repeat region of the 120-kDa protein gene was expressed as a GST fusion protein. The estimated molecular size of the fusion protein on SDS gel was approximately 140-kDa, which is much larger than the predicted molecular mass of the entire E. canis 120-kDa protein, which is only 73.6 kDa based on the amino acids deduced from the DNA sequence (FIG. 9). Mouse antibodies to the recombinant 120-kDa protein reacted with a 120-kDa protein of E. canis (FIG. 10). Canine anti- E. canis sera reacted with the recombinant E. canis 120-kDa protein also (FIG. 11).

EXAMPLE 16
Discussion

Although Ehrlichia spp. are obligately intracellular bacteria, neither the adhesin or the invasin gene of ehrlichiae has been identified. The 120-kDa protein gene of E. chaffeensis was previously cloned and sequenced (Yu 1997). The E. chaffeensis 120-kDa protein was recently demonstrated to be an outer membrane protein that is preferentially expressed on the dense-core ultrastructural form of E. chaffeensis, but not on the reticular cell. A non-invasive, non-adherent strain of E. coli expressing the 120-kDa protein acquired the ability of adherence and entry into cultured mammalian cells. These results suggest that the 120-kDa protein could be an adhesin or invasin, and therefore it would be a vaccine candidate.

Ehrlichia canis and E. chaffeensis are genetically and antigenically closely related species. The homologies between the E. canis and E. chaffeensis are 98% for the 16S rRNA gene and 89% for the nadA gene (Yu 1997). Since the 120-kDa protein appears to be important in the attachment and entry of E. chaffeensis and the two Ehrlichia species are closely related, it was hypothesized that an analogue of the 120-kDa protein gene of E. chaffeensis might exist in E. canis and possess similar biological functions. The hypothesis was confirmed by PCR amplification of the E. canis 120 kDa protein gene with primers derived from the E. chaffeensis gene. However, the DNA homology of the 120 kDa protein gene of E. canis differed substantially from the homologous gene of E. chaffeensis. The homology of the 120-kDa protein genes of E. canis and E. chaffeensis is only 30%. The low homology of the genes of these two Ehrlichia species may explain the lack of hybridization by Southern blotting of E. canis DNA with a E. chaffeensis 120-kDa protein gene probe and the lack of PCR amplification of the E. canis gene with primers derived from the coding region of the E. chaffeensis 120-kDa protein gene. It is surprising that the non-coding sequences flanking the 120-kDa protein genes are more conserved than the coding sequences of the 120-kDa protein genes of E. canis and E. chaffeensis. From an evolutionary point of view, the coding sequence which is under selection pressure would be expected to be more conserved than the non-coding sequence in which mutation would not be expected to affect survival of the organism.

Although the homology of the 120 kDa protein genes of E. canis and E. chaffeensis are not significant, it was believed that the E. canis gene is the homologue of the E. chaffeensis 120-kDa protein considering that they are located in similar positions in the respective genome; they are 30% homologous; and especially they share common motifs in the repeat region. However, both the amino acid sequence and the number of repeats in the 120-kDa-protein genes of *E. chaffeensis* and *E. canis* are different. The *E. chaffeensis* 120-kDa protein contains 4 repeats with 80 amino acids each, and the *E. canis* 120-kDa protein contains 14 repeats with 36 amino acids each. However, the repeats in both proteins are hydrophilic and are predicted to be surface-exposed. Even the total number of surface-exposed regions in the repeats of the two proteins is very close in spite of the difference in the repeat number. The repeat units of both proteins share a common motif consisting of identical amino acids that are hydrophilic and form the core of the surface exposed regions of these proteins. The repeat units of both proteins are rich in serine and glutamic acid. Serine and glutamic acid each comprise 19% of the amino acids of the *E. canis* repeat unit. Glutamic acid and serine comprise of 22% and 15% of the amino acids of the *E. chaffeensis* repeat units, respectively. Although a signal sequence was not found at the N-terminus of the deduced amino acids of the 120-kDa protein of *E. canis* by the PSORT protein localization prediction program, however, it was believed that the 120-kDa protein of *E. canis* is a surface protein similar to the *E. chaffeensis* 120-kDa protein in which the signal sequence is also absent (Yu 1997).

Like the *E. chaffeensis* 120-kDa protein gene, the predicted molecular mass of the *E. canis* 120-kDa protein is much larger than the molecular size estimated by the electrophoretic mobility of the protein by SDS-PAGE. The same phenomenon has been reported for other proteins containing repeat domains, including *Anaplasma marginale* (Allred DR et al 1990), Plasmodium (Kemp D. J. 1987), *Staphylococcus aureus* (Hollingshead 1986, Signas 1989), and the human granulocytic ehrlichia (HGE) 100-kDa and 130-kDa proteins (Storey J. R. 1998). The repeat units of the HGE 100- and 130-kDa proteins have sequences in common with those of the *E. chaffeensis* 120-kDa protein (Storey, 1998 ). The aberrant migration of the 120-kDa proteins of *E. canis* and *E. chaffeensis* is not caused by the high percentages of certain amino acids since the molecular weight of the protein is larger than the total molecular weight of the predicted amino acids. The aberrant migration of the 120-kDa protein is possibly related to post-translational modification of the protein such as glycosylation. The post translational modification of the 120-kDa protein of *E. canis* and *E. chaffeensis* is currently under investigation. Since the 120-kDa protein of *E. chaffeensis* was differentially expressed in different ultrastructural forms of *E. chaffeensis*, this protein may play a role in the pathogenesis of *E. chaffeensis* infection. Whether or not the *E. canis* 120-kDa protein is preferentially expressed in the dense core cell of *E. canis* is under investigation. Although the 120 kDa protein gene of most *E. canis* strains was not sequenced completely, it is reasonable to assume that the sequence of the 120 kDa protein gene is identical among all strains of *E. canis* based on the fact that the known sequence including the non-repeat regions as well as the first and the last repeats are identical among strains of *E. canis* and the fact that all *E. canis* strains have same number of repeats. The highly homology of DNA sequence and identical number of repeats of the 120 kDa protein gene among the strains of *E. canis* indicated that *E. canis* strains are genetically less diversified than *E. chaffeensis* in which the number of repeats of the 120 kDa protein gene differed among strains.

The following references were cited herein.

1. Allred, D. R., et al., 1990. Proc. Natl. Aca. Sci. USA. 87:3220–4.
2. Anderson, B. E., et al., 1991. J Clin Microbiol 29:2838–2842.
3. Anderson, B. E., et al., 1992. Int J Syst Bacteriol 42:299–302.
4. Bakken, J. S., et al., 1994. JAMA. 272:212–8.
5. Buhles, W. C. Jr., et al., 1974. J Infect. Dis 130:357–367.
6. Chen, S. M., et al., 1994. J Clin Microbiol 32:589–95.
7. Chen, S. M, et al., 1994. Am J Trop Med Hyg 50:52–58.
8. Dawson J. E., et al., 1991. J Infect Dis 163:564–567.
9. Fishbein, D. B., et al., 1987. JAMA. 257:3100–4.
10. Greene C. E., et al., 1984. Canine ehrlichiosis. p545–561. In C. E. Greene (ed), Clinical microbiology and infectious diseases of the dog and cat. The W. B. Saunders Co., Philadelphia.
11. Groves, M. G., et al., 1975. Am J Veterinary Research. 36:937–40.
12. Hollingshead, S. K., et al., 1986. J Biol Chem 261:1677–86.
13. Kemp, D. J., et al., 1987. Annu. Rev. Microbiol. 41:181–208.
14. Jameson, B. A., et al., 1988. CABIO, 4:181–186.
15. Klein, P., et al., 1985. Biochem. Biophys. Acta, 815:468–76.
16. Lewis, G. E. Jr., et al., 1977. American Journal of Veterinary Research. 38:1953–5.
17. Maeda, K., N. et al., 1987. N. Engl. J. Med. 316:853–856.
18. McGeoch D. J., 1985. Virus Research 3, 271–86.
19. Perez, M., et al., 1996. J Clin Microbiol 34:2133–9.
20. Rothbard, J. B., et al., 1988. The EMBO J 7:93–100.
21. Signas, C., et al., 1989. Proc. Natl. Acad. Sci. USA 86:699–703.
22. Storey, J. R., et al., 1998. Infect, Immun. 66:1356–63.
23. von Heijne G. 1986. Nucl. Acids Res. 14: 4683–90.
24. Walker, J. S., et al., 1970. J Am Vet Med Assoc. 157:43–55.
25. Yu, X-J., et al., 1996. Gene. 184:149–54.
26. Yu X-J., et al., 1997. FEMS Microbiol Letters. 154:53–8.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. An isolated nucleic acid segment encoding a 120 kDa protein of *Ehrlichia canis*, wherein said protein is immunoreactive with anti-*Ehrlichia canis* serum, and wherein said protein has an amino acid sequence of SEQ ID NO: 8.

2. The nucleic acid segment of claim 1, wherein said segment has the sequence of SEQ ID NO: 7.

3. A vector comprising the nucleic acid segment of claim 1.

4. The vector of claim 3, wherein said vector is an expression vector capable of expressing a polypeptide encoded by SEQ ID NO: 7 when said expression vector is introduced into a cell.

5. A host cell comprising the nucleic acid segment of claim 1.

* * * * *

UNITED STATES PATENT AND TRADEMARK OFFICE
CERTIFICATE OF CORRECTION

PATENT NO. : 6,043,085
DATED : March 28, 2000
INVENTOR(S) : Xue-Jie Yu, et al

It is certified that error appears in the above-identified patent and that said Letters Patent is hereby corrected as shown below:

In Column 1, line 55, "Trop Med Hyg" should read --Trop. Med. Hyg.--.

In Column 3, line 18, "shows" should read --show--.

In Column 3, line 26, "shows" should read --show--.

In Column 3, line 31, "in" should read --on--.

In Column 4, line 2, "[B. D. Hames" should read --(B. D. Hames--.

In Column 4, line 3, "(1985)]" should read --(1985))-- and "[B. D. Hames" should read --(B. D. Hames--.

In Column 4, line 4, "(1984)]" should read --(1984))--.

In Column 4, line 5, "(1986)]" should read --(1986))--.

In Column 4, line 6, "(1986)]" should read --(1986))--.

In Column 9, line 10, "(e. g." should read --(e. g,--.

UNITED STATES PATENT AND TRADEMARK OFFICE
CERTIFICATE OF CORRECTION

PATENT NO. : 6,043,085
DATED : March 28, 2000
INVENTOR(S) : Xue-Jie Yu, et al

It is certified that error appears in the above-identified patent and that said Letters Patent is hereby corrected as shown below:

In Column 11, line 10, please delete the comma after the word "salts".

In Column 11, line 36, please delete the comma after the word "infusion".

In Column 19, line 34, "Allred DR" should read --Allred, D. R.--.

In Column 19, line 35, "et al 1990" should read --et al., 1990--.

In Column 19, line 38, please insert a comma after the word "Storey".

In Column 19, line 40, please delete the comma after the word "Storey,".

In Column 20, line 7, "J Clin Microbiol" should read --J. Clin. Microbiol.--.

In Column 20, line 9, "Int J Syst Bacteriol" should read --Int. J. Syst. Bacteriol.--.

UNITED STATES PATENT AND TRADEMARK OFFICE
CERTIFICATE OF CORRECTION

PATENT NO. : 6,043,085
DATED : March 28, 2000
INVENTOR(S) : Xue-Jie Yu, et al

It is certified that error appears in the above-identified patent and that said Letters Patent is hereby corrected as shown below:

In Column 20, line 14, "J Clin Microbiol" should read --J. Clin. Microbiol.--.

In Column 20, line 15, "Am J Trop Med Hyg" should read --Am. J. Trop. Med. Hyg.--.

In Column 20, line 16, "J Infect Dis" should read --J. Infect. Dis.--.

In Column 20, line 23, "Am J Veterinary" should read --Am. J. Veterinary--.

In Column 20, line 25, "J Biol Chem" should read --J. Biol. Chem.--.

UNITED STATES PATENT AND TRADEMARK OFFICE
CERTIFICATE OF CORRECTION

PATENT NO. : 6,043,085
DATED : March 28, 2000
INVENTOR(S) : Xue-Jie Yu, et al

It is certified that error appears in the above-identified patent and that said Letters Patent is hereby corrected as shown below:

In Column 20, line 39, "J Clin Microbiol" should read --J. Clin. Microbiol.--.

In Column 20, line 40, "The EMBO J" should read --The EMBO. J.--.

In Column 20, line 45, "J Am Vet Med Assoc." should read --J. Am. Vet. Med. Assoc.--.

Signed and Sealed this

Twenty-fourth Day of April, 2001

NICHOLAS P. GODICI

Attest:

Attesting Officer

Acting Director of the United States Patent and Trademark Office

SEQUENCE LISTING

<160> NUMBER OF SEQ ID NOS: 15

<210> SEQ ID NO 1
<211> LENGTH: 21
<212> TYPE: DNA
<213> ORGANISM: artificial sequence
<220> FEATURE:
<221> NAME/KEY: primer_bind
<222> LOCATION: -341..-321
<223> OTHER INFORMATION: Forward primer pxcf2-2 used to amplify the E. canis gene encoding the 120 kDa immunoreactive protein.

<400> SEQUENCE: 1
gaaacaatct accgggcata c                    21

<210> SEQ ID NO 2
<211> LENGTH: 21
<212> TYPE: DNA
<213> ORGANISM: artificial sequence
<220> FEATURE:
<221> NAME/KEY: primer_bind
<222> LOCATION: -110..-56
<223> OTHER INFORMATION: Forward primer pxcf3 used to amplify the E. canis gene encoding the 120 kDa immunoreactive protein.

<400> SEQUENCE: 2
gagaattgat tgtggagttg g                    21

<210> SEQ ID NO 3
<211> LENGTH: 21
<212> TYPE: DNA
<213> ORGANISM: artificial sequence
<220> FEATURE:
<221> NAME/KEY: primer_bind
<222> LOCATION: 38..59
<223> OTHER INFORMATION: Forward primer pxcf3b used to amplify the E. canis gene encoding the 120 kDa immunoreactive protein.

<400> SEQUENCE: 3
cagcaagagc aagaagatga c                    21

<210> SEQ ID NO 4
<211> LENGTH: 21
<212> TYPE: DNA
<213> ORGANISM: artificial sequence
<220> FEATURE:
<221> NAME/KEY: primer_bind
<222> LOCATION: 1258..1237
<223> OTHER INFORMATION: Reverse primer pxar5 used to amplify the E. canis gene encoding the 120 kDa immunoreactive protein.

<400> SEQUENCE: 4
atctttctct acaacaaccg g                    21

<210> SEQ ID NO 5
<211> LENGTH: 21
<212> TYPE: DNA
<213> ORGANISM: artificial sequence
<220> FEATURE:
<221> NAME/KEY: primer_bind
<222> LOCATION: 1454..1433
<223> OTHER INFORMATION: Reverse primer pxar4 used to amplify the E. canis gene encoding the 120 kDa immunoreactive protein.

<400> SEQUENCE: 5
acataacatt ccactttcaa a                    21

-continued

<210> SEQ ID NO 6
<211> LENGTH: 21
<212> TYPE: DNA
<213> ORGANISM: artificial sequence
<220> FEATURE:
<221> NAME/KEY: primer_bind
<222> LOCATION: 49..70
<223> OTHER INFORMATION: Reverse primer pxar3 used to amplify the E. canis gene encoding the 120 kDa immunoreactive protein.

<400> SEQUENCE: 6
aaacaaaaaa atagcaagca a 21

<210> SEQ ID NO 7
<211> LENGTH: 2489
<212> TYPE: DNA
<213> ORGANISM: Ehrlichia canis
<220> FEATURE:
<222> LOCATION: -340..2149
<223> OTHER INFORMATION: Nucleotide sequence of gene encoding 120kDa immunoreactive protein

<400> SEQUENCE: 7
aaacaatcta ccgggcatac ttcaacacaa tcagtatatt tgcatcttat gcacttatcg 60
gtaacgaagt gtgtcattac agagttatta ataataaagt aaccattttt attgtaatgt 120
tttttcttgc caagttcaat taatttattg tttacataag gtataaatgc ggattatggt 180
taaattatgc atgtcgtaag tataaaataa gttgataagt gttttgttat atcctaatag 240
atataggagg cattggttct atataaatgt tattttatga taaataatta atttttaaca 300
ggatgaattt gtgcaatgta tttaaattaa gaggattttt atggatattg ataacaataa 360
tgtgactaca tcaagtacgc aagataaaag tgggaattta atggaagtga ttatgcgtat 420
attaaatttt ggtaataatt cagatgagaa agtaagcaat gaagacacta aagttcttgt 480
agagagttta caacctgctg tgaatgacaa tgtaggaaat ccatcaagtg aagttggtaa 540
agaagaaaat gctcctgaag ttaaagcgga agatttgcaa cctgctgtag atggtagtgt 600
agaacattca tcaagtgaag ttgggaaaaa agtatctgaa actagtaaag aggaaagtac 660
tcctgaagtt aaagcagaag atttgcaacc tgctgtagat ggtagtatag aacattcatc 720
aagtgaagtt ggagaaaaag tatctaaaac tagtaaagag gaaagtactc ctgaagttaa 780
agcagaagat ttgcaacctg ctgtagatga tagtgtggaa cattcatcaa gtgaagttgg 840
agaaaaagta tctgaaacta gtaaagagga aaatactcct gaagttaaag cagaagattt 900
gcaacctgct gtagatggta gtatagaaca ttcatcaagt gaagttggag aaaaagtatc 960
taaaactagt aaagaagaaa gtactcctga agttaaagca gaagatttgc aacctgctgt 1020
agatgatagt gtggaacatt catcaagtga agttggagaa aaagtatctg aaactagtaa 1080
agaagaaaat actcctgaag ttaaagcgga agatttgcaa cctgctgtag atggtagtgt 1140
agaacattca tcaagtgaag ttgggaaaaa agtatctgaa actagtaaag aggaaagtac 1200
tcctgaagtt aaagcagaag atttgcaacc tgctgtagat gatagtgtgg aacattcatc 1260
aagtgaagtt ggagaaaaag tatctgaaac tagtaaagag gaaaatactc ctgaagttag 1320
agcagaagat ttgcaacctg ctgtagatgg tagtgtagaa cattcatcaa gtgaagttgg 1380
agaaaaagta tctgaaacta gtaaagagga aagtactcct gaagttaaag cagaagattt 1440
gcaacctgct gtagatagta gtatagaaca ttcatcaagt gaagttggga aaaaagtatc 1500
tgaaactagt aaagaggaaa gtactcctga agttaaagca gaagatttgc aacctgctgt 1560

-continued

```
agatggtagt gtagaacatt catcaagtga agttggagaa aaagtatctg aaactagtaa    1620
agaggaaaat actcctgaag ttaaagcaga agatttgcaa cctgctgtag atggtagtgt    1680
agaacattca tcaagtgaag ttggagaaaa agtatctgaa actagtaaag aggaaaatac    1740
tcctgaagtt aaagcggaag atttgcaacc tgctgtagat ggtagtgtag aacattcatc    1800
aagtgaagtt ggagaaaaag tatctgaaac tagtaaggaa gaaagtactc ctgaagttaa    1860
agcggaagat ttgcaacctg ctgtagatgg tagtgtggaa cattcatcaa gtgaagttgg    1920
agaaaaagta tctgagacta gtaaagaaga agtactcct gaagttaaag cggaagattt     1980
gcaacctgct gtagatggta gtgtggaaca ttcatcaagt gaagttggag aaaaagtatc    2040
tgagactagt aaagaggaaa gtactcctga agttaaagcg gaagtacagc ctgttgcaga    2100
tggtaatcct gttcctttaa atcctatgcc ttcaattgat aatattgata ctaatataat    2160
attccattac cataaagact gtaaaaaagg ttcagctgta ggaacagatg aaatgtgttg    2220
tcctgtatca gaattaatgg ctggggaaca tgttcatatg tatggaattt atgtctatag    2280
agttcaatca gtaaaggatt taagtggtgt atttaatata gatcattcta catgtgattg    2340
taatttagat gtttattttg taggatacaa ttctttttact aacaaagaaa cagttgattt    2400
aatataatat tgtagtacgt aagctttata aaattgtata ttgaatagca agtaatgcta    2460
atgcagtatt gcttgctatt ttttttgttt                                     2489
```

<210> SEQ ID NO 8
<211> LENGTH: 688
<212> TYPE: PRT
<213> ORGANISM: Ehrlichia canis
<220> FEATURE:
<223> OTHER INFORMATION: Amino acid sequence of 120 kDa immunoreactive
      protein.

<400> SEQUENCE: 8

```
Met Asp Ile Asp Asn Asn Asn Val Thr Thr Ser Ser Thr Gln Asp
                 5                  10                  15

Lys Ser Gly Asn Leu Met Glu Val Ile Met Arg Ile Leu Asn Phe
                20                  25                  30

Gly Asn Asn Ser Asp Glu Lys Val Ser Asn Glu Asp Thr Lys Val
                35                  40                  45

Leu Val Glu Ser Leu Gln Pro Ala Val Asn Asp Asn Val Gly Asn
                50                  55                  60

Pro Ser Ser Glu Val Gly Lys Glu Glu Asn Ala Pro Glu Val Lys
                65                  70                  75

Ala Glu Asp Leu Gln Pro Ala Val Asp Gly Ser Val Glu His Ser
                80                  85                  90

Ser Ser Glu Val Gly Lys Lys Val Ser Glu Thr Ser Lys Glu Glu
                95                  100                 105

Ser Thr Pro Glu Val Lys Ala Glu Asp Leu Gln Pro Ala Val Asp
                110                 115                 120

Gly Ser Ile Glu His Ser Ser Ser Glu Val Gly Glu Lys Val Ser
                125                 130                 135

Lys Thr Ser Lys Glu Glu Ser Thr Pro Glu Val Lys Ala Glu Asp
                140                 145                 150

Leu Gln Pro Ala Val Asp Asp Ser Val Glu His Ser Ser Ser Glu
                155                 160                 165

Val Gly Glu Lys Val Ser Glu Thr Ser Lys Glu Glu Asn Thr Pro
                170                 175                 180
```

-continued

```
Glu Val Lys Ala Glu Asp Leu Gln Pro Ala Val Asp Gly Ser Ile
                185                 190                 195

Glu His Ser Ser Ser Glu Val Gly Lys Val Ser Lys Thr Ser
            200                 205                 210

Lys Glu Glu Ser Thr Pro Glu Val Lys Ala Glu Asp Leu Gln Pro
                215                 220                 225

Ala Val Asp Asp Ser Val Glu His Ser Ser Glu Val Gly Glu
            230                 235                 240

Lys Val Ser Glu Thr Ser Lys Glu Glu Asn Thr Pro Glu Val Lys
                245                 250                 255

Ala Glu Asp Leu Gln Pro Ala Val Asp Gly Ser Val Glu His Ser
                260                 265                 270

Ser Ser Glu Val Gly Lys Lys Val Ser Glu Thr Ser Lys Glu Glu
                275                 280                 285

Ser Thr Pro Glu Val Lys Ala Glu Asp Leu Gln Pro Ala Val Asp
                290                 295                 300

Asp Ser Val Glu His Ser Ser Glu Val Gly Glu Lys Val Ser
            305                 310                 315

Glu Thr Ser Lys Glu Glu Asn Thr Pro Glu Val Arg Ala Glu Asp
                320                 325                 330

Leu Gln Pro Ala Val Asp Gly Ser Val Glu His Ser Ser Glu
            335                 340                 345

Val Gly Glu Lys Val Ser Glu Thr Ser Lys Glu Glu Ser Thr Pro
                350                 355                 360

Glu Val Lys Ala Glu Asp Leu Gln Pro Ala Val Asp Ser Ser Ile
                365                 370                 375

Glu His Ser Ser Glu Val Gly Lys Lys Val Ser Glu Thr Ser
            380                 385                 390

Lys Glu Glu Ser Thr Pro Glu Val Lys Ala Glu Asp Leu Gln Pro
                395                 400                 405

Ala Val Asp Gly Ser Val Glu His Ser Ser Glu Val Gly Glu
            410                 415                 420

Lys Val Ser Glu Thr Ser Lys Glu Glu Asn Thr Pro Glu Val Lys
                425                 430                 435

Ala Glu Asp Leu Gln Pro Ala Val Asp Gly Ser Val Glu His Ser
                440                 445                 450

Ser Ser Glu Val Gly Glu Lys Val Ser Glu Thr Ser Lys Glu Glu
            455                 460                 465

Asn Thr Pro Glu Val Lys Ala Glu Asp Leu Gln Pro Ala Val Asp
                470                 475                 480

Gly Ser Val Glu His Ser Ser Glu Val Gly Glu Lys Val Ser
            485                 490                 495

Glu Thr Ser Lys Glu Glu Ser Thr Pro Glu Val Lys Ala Glu Asp
                500                 505                 510

Leu Gln Pro Ala Val Asp Gly Ser Val Glu His Ser Ser Glu
            515                 520                 525

Val Gly Glu Lys Val Ser Glu Thr Ser Lys Glu Glu Ser Thr Pro
                530                 535                 540

Glu Val Lys Ala Glu Asp Leu Gln Pro Ala Val Asp Gly Ser Val
                545                 550                 555

Glu His Ser Ser Ser Glu Val Gly Glu Lys Val Ser Glu Thr Ser
            560                 565                 570

Lys Glu Glu Ser Thr Pro Glu Val Lys Ala Glu Val Gln Pro Val
```

```
                    575                 580                 585

Ala Asp Gly Asn Pro Val Pro Leu Asn Pro Met Pro Ser Ile Asp
                590                 595                 600

Asn Ile Asp Thr Asn Ile Ile Phe His Tyr His Lys Asp Cys Lys
                605                 610                 615

Lys Gly Ser Ala Val Gly Thr Asp Glu Met Cys Cys Pro Val Ser
                620                 625                 630

Glu Leu Met Ala Gly Glu His Val His Met Tyr Gly Ile Tyr Val
                635                 640                 645

Tyr Arg Val Gln Ser Val Lys Asp Leu Ser Gly Val Phe Asn Ile
                650                 655                 660

Asp His Ser Thr Cys Asp Cys Asn Leu Asp Val Tyr Phe Val Gly
                665                 670                 675

Tyr Asn Ser Phe Thr Asn Lys Glu Thr Val Asp Leu Ile
                680                 685

<210> SEQ ID NO 9
<211> LENGTH: 406
<212> TYPE: PRT
<213> ORGANISM: Ehrlichia chaffeensis
<220> FEATURE:
<223> OTHER INFORMATION: Amino acid sequence of 120 kDa protein used to
      determine homology with E. canis 120 kDa protein.
<300> PUBLICATION INFORMATION:
<301> AUTHORS: Walker, David H.
      Yu, Xue-Jie
<302> TITLE: Immunodominant 120 kDa Surface-Exposed Adhesion
      Protein Genes of Ehrlichia chaffeensis
<310> PATENT DOCUMENT NUMBER: US 08/656,034
<311> PATENT FILING DATE: 1996-05-31

<400> SEQUENCE: 9

Met Asp Ile Asp Asn Ser Asn Ile Ser Thr Ala Asp Ile Arg Ser
                  5                  10                  15

Asn Thr Asp Gly Leu Ile Asp Ile Ile Met Arg Ile Leu Gly Phe
                 20                  25                  30

Gly Asn Lys Asn Ile Val Gln Pro Gln Asp Leu Gly Ser Glu Ile
                 35                  40                  45

Tyr Gln Gln Glu Gln Glu Asp Asp Thr Val Ser Gln Pro Ser Leu
                 50                  55                  60

Glu Pro Phe Val Ala Glu Ser Glu Val Ser Lys Val Glu Gln Glu
                 65                  70                  75

Lys Thr Asn Pro Glu Val Leu Ile Lys Asp Leu Gln Asp Val Ala
                 80                  85                  90

Ser His Glu Ser Gly Val Ser Asp Gln Pro Ala Gln Val Val Thr
                 95                 100                 105

Glu Arg Glu Asn Glu Ile Glu Ser His Gln Gly Glu Thr Glu Lys
                110                 115                 120

Glu Ser Gly Ile Thr Glu Ser His Gln Lys Glu Asp Glu Ile Val
                125                 130                 135

Ser Gln Ser Ser Ser Glu Pro Phe Val Ala Glu Ser Glu Val Ser
                140                 145                 150

Lys Val Glu Gln Glu Glu Thr Asn Pro Glu Val Leu Ile Lys Asp
                155                 160                 165

Leu Gln Asp Val Ala Ser His Glu Ser Gly Val Ser Asp Gln Pro
                170                 175                 180

Ala Gln Val Val Thr Glu Arg Glu Ser Glu Ile Glu Ser His Gln
                185                 190                 195
```

-continued

```
Gly Glu Thr Glu Lys Glu Ser Gly Ile Thr Glu Ser His Gln Lys
                200                 205                 210

Glu Asp Glu Ile Val Ser Gln Ser Ser Ser Glu Pro Phe Val Ala
                215                 220                 225

Glu Ser Glu Val Ser Lys Val Glu Gln Glu Glu Thr Asn Pro Glu
                230                 235                 240

Val Leu Ile Lys Asp Leu Gln Asp Val Ala Ser His Glu Ser Gly
                245                 250                 255

Val Ser Asp Gln Pro Ala Gln Val Val Thr Glu Arg Glu Ser Glu
                260                 265                 270

Ile Glu Ser His Gln Gly Glu Thr Glu Lys Glu Ser Gly Ile Thr
                275                 280                 285

Glu Ser His Gln Lys Glu Asp Glu Ile Val Ser Gln Pro Ser Ser
                290                 295                 300

Glu Pro Phe Val Ala Glu Ser Glu Val Ser Lys Val Glu Gln Glu
                305                 310                 315

Glu Thr Asn Pro Glu Val Leu Ile Lys Asp Leu Gln Asp Val Ala
                320                 325                 330

Ser His Glu Ser Gly Val Ser Asp Gln Pro Ala Gln Val Val Thr
                335                 340                 345

Glu Arg Glu Ser Glu Ile Glu Ser His Gln Gly Glu Thr Glu Lys
                350                 355                 360

Glu Ser Gly Ile Thr Glu Ser His Gln Lys Glu Asp Glu Ile Val
                365                 370                 375

Ser Gln Pro Ser Ser Glu Pro Phe Val Ala Glu Ser Glu Val Ser
                380                 385                 390

Lys Val Glu Gln Glu Lys Thr Asn Pro Glu Ile Leu Val Glu Asp
                395                 400                 405

Leu
```

```
<210> SEQ ID NO 10
<211> LENGTH: 367
<212> TYPE: PRT
<213> ORGANISM: Ehrlichia canis
<220> FEATURE:
<223> OTHER INFORMATION: Amino acid sequence of 120 kDa protein used to
      determine homology of E. chaffeensis 120 kDa
      proteins.

<400> SEQUENCE: 10

Met Asp Ile Asp Asn Asn Asn Val Thr Thr Ser Ser Thr Gln Asp
                5                   10                  15

Lys Ser Gly Asn Leu Met Glu Val Ile Met Arg Ile Leu Asn Phe
                20                  25                  30

Gly Asn Asn Ser Asp Glu Lys Val Ser Asn Glu Asp Thr Lys Val
                35                  40                  45

Leu Val Glu Ser Leu Gln Pro Ala Val Asn Asp Asn Val Gly Asn
                50                  55                  60

Pro Ser Ser Glu Val Gly Lys Glu Glu Asn Ala Pro Glu Val Lys
                65                  70                  75

Ala Glu Asp Leu Gln Pro Ala Val Asp Gly Ser Val Glu His Ser
                80                  85                  90

Ser Ser Glu Val Gly Lys Lys Val Ser Glu Thr Ser Lys Glu Glu
                95                  100                 105

Ser Thr Pro Glu Val Lys Ala Glu Asp Leu Gln Pro Ala Val Asp
```

```
                       110                 115                 120

Gly Ser Ile Glu His Ser Ser Glu Val Gly Lys Val Ser
                125                 130                 135

Lys Thr Ser Lys Glu Glu Ser Thr Pro Glu Val Lys Ala Glu Asp
                140                 145                 150

Leu Gln Pro Ala Val Asp Asp Ser Val Glu His Ser Ser Glu
                155                 160                 165

Val Gly Glu Lys Val Ser Glu Thr Ser Lys Glu Glu Asn Thr Pro
                170                 175                 180

Glu Val Lys Ala Glu Asp Leu Gln Pro Ala Val Asp Gly Ser Ile
                185                 190                 195

Glu His Ser Ser Ser Glu Val Gly Glu Lys Val Ser Lys Thr Ser
                200                 205                 210

Lys Glu Glu Ser Thr Pro Glu Val Lys Ala Glu Asp Leu Gln Pro
                215                 220                 225

Ala Val Asp Asp Ser Val Glu His Ser Ser Glu Val Gly Glu
                230                 235                 240

Lys Val Ser Glu Thr Ser Lys Glu Glu Asn Thr Pro Glu Val Lys
                245                 250                 255

Ala Glu Asp Leu Gln Pro Ala Val Asp Gly Ser Val Glu His Ser
                260                 265                 270

Ser Ser Glu Val Gly Lys Val Ser Glu Thr Ser Lys Glu Glu
                275                 280                 285

Ser Thr Pro Glu Val Lys Ala Glu Asp Leu Gln Pro Ala Val Asp
                290                 295                 300

Asp Ser Val Glu His Ser Ser Glu Val Gly Glu Lys Val Ser
                305                 310                 315

Glu Thr Ser Lys Glu Glu Asn Thr Pro Glu Val Arg Ala Glu Asp
                320                 325                 330

Leu Gln Pro Ala Val Asp Gly Ser Val Glu His Ser Ser Glu
                335                 340                 345

Val Gly Glu Lys Val Ser Glu Thr Ser Lys Glu Glu Ser Thr Pro
                350                 355                 360

Glu Val Lys Ala Glu Asp Leu
                365

<210> SEQ ID NO 11
<211> LENGTH: 30
<212> TYPE: PRT
<213> ORGANISM: Ehrlichia chaffeensis
<220> FEATURE:
<222> LOCATION: 218..247
<223> OTHER INFORMATION: Sequence of surface-exposed amino acids in a
      repeat unit of the 120 kDa protein.

<400> SEQUENCE: 11

Ser Ser Ser Glu Pro Phe Val Ala Glu Ser Glu Val Ser Lys Val
                 5                  10                  15

Glu Gln Glu Glu Thr Asn Pro Glu Val Leu Ile Lys Asp Leu Gln
                20                  25                  30

<210> SEQ ID NO 12
<211> LENGTH: 27
<212> TYPE: PRT
<213> ORGANISM: Ehrlichia canis
<220> FEATURE:
<222> LOCATION: 198..224
<223> OTHER INFORMATION: Sequence of surface-exposed amino acids in a
```

```
           repeat unit of the 120 kDa protein.

<400> SEQUENCE: 12

Ser Ser Ser Glu Val Gly Glu Lys Val Ser Lys Thr Ser Lys Glu
                 5                  10                  15

Glu Ser Thr Pro Glu Val Lys Ala Glu Asp Leu Gln
                20                  25

<210> SEQ ID NO 13
<211> LENGTH: 21
<212> TYPE: DNA
<213> ORGANISM: artificial sequence
<220> FEATURE:
<221> NAME/KEY: primer_bind
<223> OTHER INFORMATION: Forward primer used to amplify the coding
      region of the E. canis 120 kDa protein gene from nucleotides
      175 to 1793.

<400> SEQUENCE: 13
ggaaatccat caagtgaagt t                                           21

<210> SEQ ID NO 14
<211> LENGTH: 22
<212> TYPE: DNA
<213> ORGANISM: artificial sequence
<220> FEATURE:
<221> NAME/KEY: primer_bind
<223> OTHER INFORMATION: Reverse primer used to amplify the coding
      region of the E. canis 120 kDa protein gene from nucleotides
      175 to 1793.

<400> SEQUENCE: 14
ttgaaggcat aggatttaaa gg                                          22

<210> SEQ ID NO 15
<211> LENGTH: 21
<212> TYPE: DNA
<213> ORGANISM: artificial sequence
<220> FEATURE:
<222> LOCATION: 38..59
<223> OTHER INFORMATION: Oligonucleotide probe used to hybridize with
      the DNA fragments of repeats with the 5( end non-repeat
      sequence produced using Spe I restriction enzyme.

<400> SEQUENCE: 15
cgcaagataa agtgggaatt t                                           21
```